United States Patent
Decrulle et al.

(10) Patent No.: US 12,214,070 B2
(45) Date of Patent: *Feb. 4, 2025

(54) COSMETIC USE OF ENGINEERED POSTBIOTICS COMPRISING BACTERIOCINS AND/OR ENDOLYSINS

(71) Applicant: Eligo Bioscience, Paris (FR)

(72) Inventors: Antoine Decrulle, Paris (FR); Xavier Duportet, Paris (FR)

(73) Assignee: Eligo Bioscience, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/185,696

(22) Filed: Mar. 17, 2023

(65) Prior Publication Data

US 2023/0218505 A1 Jul. 13, 2023

Related U.S. Application Data

(63) Continuation of application No. 17/698,075, filed on Mar. 18, 2022, now Pat. No. 11,633,348.

(60) Provisional application No. 63/163,077, filed on Mar. 19, 2021.

(51) Int. Cl.
| | |
|---|---|
| A61K 8/99 | (2017.01) |
| A61K 35/747 | (2015.01) |
| A61K 38/16 | (2006.01) |
| A61K 38/47 | (2006.01) |
| A61P 17/00 | (2006.01) |
| A61Q 19/00 | (2006.01) |

(52) U.S. Cl.
CPC ............ *A61K 8/99* (2013.01); *A61K 35/747* (2013.01); *A61K 38/164* (2013.01); *A61K 38/47* (2013.01); *A61P 17/00* (2018.01); *A61Q 19/005* (2013.01); *A61Q 19/007* (2013.01)

(58) Field of Classification Search
None
See application file for complete search history.

(56) References Cited

U.S. PATENT DOCUMENTS

| | | |
|---|---|---|
| 8,568,714 B2 | 10/2013 | Donovan et al. |
| 11,541,106 B2 | 1/2023 | Decrulle et al. |
| 2002/0187136 A1 | 12/2002 | Loomis et al. |
| 2018/0325968 A1 | 11/2018 | Morris |
| 2019/0374621 A1 | 12/2019 | Offerhaus et al. |
| 2020/0254064 A1 | 8/2020 | Chumburidze |
| 2021/0244779 A1 | 8/2021 | O'Neill |

FOREIGN PATENT DOCUMENTS

| | | |
|---|---|---|
| CN | 103119158 B | 4/2015 |
| CN | 107412045 A | 12/2017 |
| WO | 2013/153358 A1 | 10/2013 |
| WO | 2015/005787 A1 | 1/2015 |
| WO | 2015/181534 A1 | 12/2015 |
| WO | 2017/199022 A2 | 11/2017 |

OTHER PUBLICATIONS

Aguilar-Toala et al. Postbiotics: An evolving term within the functional foods field. Trends in Food Science & Technology, 2018, 75, 105-114.

Jung et al. Lysates of a Probiotic, *Lactobacillus rhamnosus*, Can Improve Skin Barrier Function in a Reconstructed Human Epidermis Model. International Journal of Molecular Sciences, 2019, 20(17), 4289. 1-12.

Khaneghah et al. Interaction between probiotics and pathogenic microorganisms in hosts and foods: A review. Trends in Food Science and Technology, 2020, 95, 205-218.

Mohammedsaeed et al. Lactobacillus rhamnosus GG Inhibits the Toxic Effects of *Staphylococcus aureus* on Epidermal Keratinocytes. Applied and Environmental Microbiology, 2014, 80(18), 5773-5781.

Salminen et al. The International Scientific Association of Probiotics and Prebiotics (ISAPP) consensus statement on the definition and scope of postbiotics. Reviews: Gastroenterology and Hepatology, 2021, 18, 649-667.

Totte et al. Successful Treatment of Chronic *Staphylococcus aureus*-Related Dermatoses with the Topical Endolysin Staphefekt SA.100: A Report of 3 Cases. Case Reports in Dermatology, 2017, 9, 19-25.

Liu H et al. Inhibition of *S. aureus* by Lysostaphin Expressing L. plantarum WCFS1 in a Modified Genital Tract Secretion Medium. Applied and Environmental Microbiology, 2011, 77(24), 8500-8508.

Esposito, C. Surface Level Happiness. 2020. 57(11), 62-66.

Meade, E. et al. Bacteriocins, Potent Antimicrobial Peptides and the Fight again Multi Drug Resistant Species: Resistance is Futile? Antibiotics, 2020, 9(32), 1-18.

Teame et al. Paraprobiotics and Postbiotics of Probiotic Lactobacilli, Their Positive Effects on the Host and Action Mechanisms: A Review. Frontiers in Nutrition, 2020, 7, 1-16.

Chang et al. Comparative Studies of Inhibitory and Antioxidant Activities, and Organic Acids Compositions of Postbiotics Produces by Probiotic *Lactiplantibacillus plantarum* Strains Isolated from Malaysian Foods. Frontiers in Veternary Science, 2021, 7, 1-14.

Abdelrahman F et al. Phage Encoded Endolysins Antibiotics, 2021, 10, 1-29.

Malashree L. et al. Postbiotics One Step Ahead of Probiotics. Int J Curr Microbiol App Scie, 2019, 8(1), 2049-2053.

Schmelcher et al. Bacteriophage Endolysins as Novel Antimicrobials, Future Microbiology, 2012, 7(10), 1147-1171.

(Continued)

*Primary Examiner* — Nicole P Babson
(74) *Attorney, Agent, or Firm* — Arrigo, Lee, Guttman & Mouta-Bellum LLP

(57) ABSTRACT

A method for the cosmetic caring of the skin and/or mucosa, comprising applying a postbiotic composition comprising at least one postbiotic and at least one bacteriocin and/or endolysin, wherein the postbiotic is preferably a bacterial lysate preferably obtained from bacteria heterologously expressing the at least one bacteriocin and/or endolysin and wherein the postbiotic and the at least one bacteriocin and/or endolysin have a synergistic effect in the cosmetic caring method.

15 Claims, 6 Drawing Sheets

(56) References Cited

OTHER PUBLICATIONS

Mohammedsaeed et al. Lactobacillus rhamnosus GG Lysate Increases Re-Epithelialization of Keratinocyte Scratch Assays by Promoting Migration. Scientific Reports, 2015, 5:16147, 1-11.

Borysowski and Gorski. Anti-Staphylococcal Lytic Enzymes. Enzybiotics: Antibiotic Enzymes as Drugs and Therapeutics by Tomas G Villa Willey & Sons, 2010, Chapter 7, 149-172.

USPTO, Office Action in U.S. Appl. No. 17/698,091, Jul. 26, 2022, 1-9.

Allain, Thibault et al. A new lactobacilli in vivo expression system for the production and delivery of heterologous proteins at mucosal surfaces, FEMS Microbiology Letters, vol. 363, Issue 13, Jul. 2016, 1-9.

Bouslimani, Amina et al. Molecular catography of the human skin surface in 3D. Pnas. Mar. 6, 2015. E2120-E2129.

Bouslimani, Amina et al. The impact of skin care products on skin chemistry and microbiome dynamics. BMC Biology, 17, 47 (2019) 1-20. https://doi.org/10.1186/s12915-019-0660-6.

Briers, Yves et al. A standardized approach for accurate quantification of murein hydrolase activity in high thyoughput assays. Journal of Biochemical and Biophysics Methods. 2007. 531-533.

Byrd, Allyson et al. The Human Skin Microbiome. Nature Reviews Microbiology. 16, 143-155 (2018). https://doi.org/10.1038/nrmicro.2017.157.

Chrowdhury, Sreyan et al. Programmable bacteria induce durable tumor regression and systemic antitumor immunity.Nature Medicine. 1057-1063 (2019). https://doi.org/10.1038/s41591-019-0498-z.

Cotter, Paul. Bacteriocins: Developing innate immunity for food. Nature Reviews Microbiology. Oct. 2005, 3 (10), 777-788. doi:10.1038/nrmicro 1240.

Donovan, David M et al. Lysis of staphylococcal mastitis pathogens by baleriophage phi11 endolysin. FEMS Microbiol Lett. Dec. 2006; 265(1):133-9. doi: 10.1111/j.1574-6968.2006.00483.x.

Fernandez-Ruiz, Iris et al. Thousands of novel endolysins discovered in uncultured phage genomes. Frontiers in Microbiology. May 18, 2018. 1-8. https://doi.org/10.3389/fmicb.2018.01033.

Gervasi, T et al. Application of Lactobacillus johnsonii expressing phage endolysin for control of Clostridium perfringens. Letter's in Applied Microbiology. 2014. 59, 355-361.

Gervasi, Teresa et al. Expression and delivery of an endolysin to combat Clostridium perfringens. Applied Microbiology Biotechnology, 2014. 98. 2495-2505. DOI 10.1007/s00253-013-5128-.

Grice, E. et al. Topographical and temporal diversity of the human skin microbiome. Science. May 29, 2009; 324 (5931): 1190-1192. doi:10.1126/science.1171700.

Grice, Elizabeth and Julia Segre. The skin microbiome. Nat Rev Microbiol. Apr. 2011 ; 9(4): 244-253. doi:10.1038/nrmicro2537.

Gurbatri, Candice et al. Engineered probiotics for local tumor delivery of checkpoint blockade nanobodies. Sci Transl Med. Feb. 12, 2020; 12(530): . doi:10.1126/scitranslmed.aax0876.

Heenan, C.N., Growth medium for culturing probiotic bacteria for applications in vegetarian food products. LWT Food Science and Technology. (2002), 35, 171-176.

Kong, Heidi H and Julia A Segre. Skin microbiome: looking back to move forward. Journal of Investigative Dermatology (2012) 132, 933-939; doi:10.1038/jid.2011.417.

Kurtz, Caroline et al. An engineered E.coli nissle improves hyperammonemia and survival in mice and shoes does—dependent exposure in healthy humans. Science Translational Medicine. Jan. 16, 2019, 11 1-14.

Leshem Avner et al. Immune-microbiota interplay and colonization resistance in infection. Molecular Cell. May 21, 2020. 78(4). 597-613.

Liu, Huanli et al. Inhibition of *Staphylococcus aureus* by lysostaphin-expressing lactobacillus plantarum WCFS1 in a modified genital tract secretion medium. Applied and Environmental Microbiology, Dec. 2011, p. 8500-8508.

Myers, Eugene and Webb Miller. Optimal alignments in linear space. CABIOS. 4(1). 1998. 11-17.

Needleman, Saul B and Christian Wunsch. A general method applicable to the search for similarities in the amino acid sequence of two proteins. J. Mol. Biol (1970). 48, 443-453.

Ohland, Christina L and Wallace K. MacNaughton. Probiotic bacteria and intestinal epithelial barrier function. Am J Physiol Gastrointest Liver Physiol 298: G807-G819, 2010. doi:10.1152/ajpgi.00243.2009.

Sfriso, R. et al. Revealing the secret life of skin—with the microbiome you never walk alone. International Journal of Cosmetic Science, 2020, 42, 116-126.

Sorvig, Elisabeth et al. High-level, inducible gene expression in Lactobacillus sakei and Lactobacillus plantarum using versatile expression vectors. Microbiology (2005), 151, 2439-2449. DOI 10.1099/mic.0.28084-0.

Suez, Jotham et al. The pros, cons, and many unknowns of probiotics. Nature Medicine. (2019), 25, 716-729.

Turner, Mark S et al. Antimicrobial activity of lysostaphin and a Listeria monocytogenes bacteriophage endolysin produced and secreted by lactic acid bacteria. Systematic and Applied Microbiology 30 (2007) 58-67.

COSMETIC USE OF ENGINEERED POSTBIOTICS COMPRISING BACTERIOCINS AND/OR ENDOLYSINS

CROSS REFERENCE TO RELATED APPLICATIONS

This application is a divisional of U.S. application Ser. No. 17/698,075, filed Mar. 18, 2022, This application claims the benefit of U.S. application 63/163,077 filed Mar. 19, 2021, which is herein incorporated by reference in its entirety.

REFERENCE TO SEQUENCE LISTING SUBMITTED ELECTRONICALLY

The contents of the electronic sequence listing (SequenceListing_EB2020-07a_USDiv.xml; Size: 2,216 bytes; and Date of Creation: Mar. 15, 2023) is herein incorporated by reference in its entirety.

TECHNICAL FIELD

The present invention relates to methods for the cosmetic caring of the skin and/or mucosa of subjects, in particular to methods for the cosmetic treatment of sensitive skin or for the cosmetic treatment and/or prevention of body odors, and to cosmetic compositions suitable for such cosmetic caring methods.

BACKGROUND

The skin has a major role in protection from external aggressions such as environment aggressions, climatic adversities (heat, cold, etc.), pollution, mechanical aggressions (epilation, shaving, abrasive scrubbing) and chemical aggressions (detergents). This property, called the barrier function, is primarily performed by the outermost layer of the epidermis, namely the horny layer or stratum corneum.

The skin also represents a complex ecosystem on which several types of microorganisms, such as bacteria and fungi, proliferate. These microorganisms constitute the skin flora, also called skin microbiota.

The skin microbiota, made up of millions of commensal microorganisms, e.g., 1 million/cm$^2$, is the second largest microbiota of the human body in mass (Byrd et al. (2018) Nat. Rev. Microbiol. 16:143-155). Cutaneous bacteria belong to four main phyla among the thirty-six known (Kong et al. (2012) J. Investig. Dermatol. 132:933-939). The average skin body distribution of these main bacteria phyla, detected on 20 diverse skin sites of 10 healthy individuals, were found to be Actinobacteria at 51.8%, Firmicutes at 24.4%, Proteobacteria at 16.5% and Bacteroidetes at 6.3% (Grice et al. (2009) Science 324:1190-1192; Bouslimani et al. (2015) Proc. Natl. Acad. Sci. 112: E2120-E2129).

Skin microbiota is involved in the maintenance of a healthy cutaneous barrier. For example microorganisms help to maintain the skin barrier, the immune system and limit unfavorable microorganism growth (Sfriso et al. (2019) Int. J. Cosmet. Sci. 42:116-126). However, an imbalance in skin microbiota, called dysbiosis, is correlated with non-pathological conditions, such as sensitive and dry skins (Grice and Segre (2011) Nat. Rev. Microbiol. 449:811-818).

An important need thus exists for preventing and/or reversing such dysbiosis in order to address such non-pathological conditions of the skin.

Cosmetic products can have an important impact on skin microbiota by for example decreasing bacterial and archeal diversity (Bouslimani, A. et al. (2019). *Bmc Biol* 17, 47.). More recently, awareness of the role of microbiota led to development of cosmetic solutions with a neutral or positive impact on the skin microbiota.

US20180325968 discloses, in particular, a product comprising a composition of prebiotic lipids and a composition containing probiotics such as *Bacillus licheniformis, Bifidobacterium breve, Bifidobacterium infantis, Lactobacillus fermentum, Lactobacillus plantarum, Lactobacillus rhamnosus, Lactobacillus sakei, Lactobacillus paracasei, Staphylococcus epidermidis*, and *Staphylococcus xylosus*, for correcting a dysbiosis or for maintaining the balance of the resident beneficial commensal flora.

CN107412045 is about a prebiotic skincare mask comprising, in particular, alpha glucooligosaccharide, inulin, a yeast, and a bacterium of the genus *Lactobacillus*, for reinforcing the presence of a healthy skin flora and preventing the colonization of the skin by pathogens.

WO2015/005787 discloses a composition for skin treatment comprising an anti-inflammatory compound and a compound specifically targeting a bacterial cell such as *S. aureus*, said compound being typically an endolysin.

Nevertheless, there is an ever-increasing need among consumers for cosmetic care respectful of their skin and especially of their skin commensal flora while being active in eliminating unfavorable bacteria and maintaining or restoring the balance of the bacterial skin and/or mucosal microbiota.

Accordingly, a need exists to provide new cosmetically active ingredients which are active on the microbial skin flora, particularly by protecting and/or stimulating the commensal flora, and which enable elimination of unfavorable bacteria and the maintenance and/or restoration of the balance of the bacterial flora of the skin and/or mucous membranes.

The present invention meets this need.

Probiotics have a large panel of beneficial interactions with human health among which:
  preventing or decreasing infection by pathogens through colonization resistance (Leshem et al. (2020) Mol Cell 78:597-613; Cotter et al. (2005) Nat Rev Microbiol 3:777-799),
  host immunomodulation (reviewed in Suez et al. (2019) Nat Med 25:716-729),
  improving barrier function (reviewed in Ohland and MacNaughton (2010) Am J Physiol-gastr L 293: G807-G819), and
  potential modulation of host microbiota.

Because they have been used for years and are generally regarded as safe, probiotics also have been engineered in order to increase their therapeutic potential by for example expressing cytokines (Allain et al. (2016) FEMS Microbiology Letters 363, fnw117), nanobodies (Gurbatri et al. (2020) Sci Transl Med 12, eaax0876; Chowdhury et al. (2019) Nat Med 25:1057-1063), enzymes (Kurtz et al/ (2019) Sci Transl Med 11, eaau7975) or bacteriocins such as endolysins (Gervasi et al. (2014) Lett Appl Microbiol 59:355-361; Gervasi et al (2014) Appl Microbiol Biot 98:2495-2505; Liu et al. (2011) Appl Environ Microb 77:8500-8508; Turner et al. (2007) Systematic and Applied Microbiology 30:58-67). However natural and engineered probiotics have several drawbacks due to their living characteristic:

storage for long time requires complex formulation,
containment strategies need to be put in place to prevent their survival in the host and in the environment,
pharmacodynamics depends not only on the dose but also on the engraftment, even transitory, and metabolic state of the probiotic population, both parameters having high inter and intra individual variability.

One way to circumvent these inconveniences is to directly administer the molecules, produced by the probiotics that act as the active substance:

metabolic enzymes,
metabolites,
bacteriocins,
bacterial structures (pili, flagels, cell wall components, DNA . . . )

Such molecules can be referred to as postbiotics.

These molecules can, in the case of secreted or freely diffusing molecules, be extracted from the media into which probiotics are growing. Examples of such molecules are Short Chain Fatty Acids (SOFA), vitamins, amino acids that are already well known microbial molecules with potential benefit for human health. This set of molecules is often referred to as cell-free supernatant (CFS). Other intracellular molecules can be extracted directly from the lysis of probiotic cells (lysate) or kept inside the inactivated (non-living) probiotic cells.

The present invention arises from the unexpected finding by the inventors that it is possible to combine the beneficial effects of probiotics with their potential to produce recombinant molecules, i.e. engineered postbiotics, from bacteria, in particular probiotic bacteria, heterologously expressing bacteriocins and/or endolysins, particularly useful for cosmetic applications.

As an example, the present inventors engineered *Lactobacillus* bacteria to produce a bacteriocin targeting specifically the bacteria *S. aureus*, and showed that a lysate produced from the mechanical disruption of these engineered probiotic cells (corresponding to an engineered postbiotic) led to highly specific and efficient lysis of *S. aureus* strains without killing commensal species and even while promoting growth of commensal species. More importantly, compared to bacteriocin alone this engineered postbiotic leads to:

a higher killing efficiency,
a faster regrowth of commensal species, and
potentially a faster return to a healthy microbiota.

Thus engineered postbiotics offer a promising alternative to address dysbiosis by specifically killing unfavorable microorganisms while at the same time promoting the growth of healthy commensal microorganisms.

To the inventor's knowledge, no engineered postbiotic has been developed so far for cosmetic applications using engineered probiotics as a source of active molecules.

SUMMARY OF THE INVENTION

The present invention thus concerns a method for the cosmetic caring of the skin and/or mucosa of a subject, comprising applying a postbiotic composition comprising at least one postbiotic, in particular at least one engineered postbiotic, and at least one bacteriocin and/or endolysin, wherein said at least one postbiotic and said at least one bacteriocin and/or endolysin have a synergistic effect in the cosmetic caring method. In a particular embodiment, said at least one postbiotic, in particular engineered postbiotic, is obtained from microorganisms, in particular bacteria, heterologously expressing said at least one bacteriocin and/or endolysin. In other words, in that embodiment, said at least one bacteriocin and/or endolysin included in said postbiotic composition is part of said postbiotic. In a particular embodiment, said at least one postbiotic, in particular engineered postbiotic, comprises at least one microbial, in particular bacterial, lysate, preferably obtained from microorganisms, in particular bacteria, heterologously expressing said at least one bacteriocin and/or endolysin and said at least one microbial, in particular bacterial, lysate and said at least one bacteriocin and/or endolysin have a synergistic effect in the cosmetic caring method. In other words, in the embodiment wherein the engineered postbiotic comprises at least one microbial lysate obtained from microorganisms heterologously expressing said at least one bacteriocin and/or endolysin, said at least one bacteriocin and/or endolysin included in said postbiotic composition is part of said microbial lysate.

The present invention also concerns a method for the cosmetic, non-therapeutic, caring of sensitive, sensitized, fragile and/or weakened skin and/or mucosa, said skin and/or mucosa being healthy skin and/or mucosa, comprising applying a postbiotic composition comprising at least one postbiotic, in particular at least one engineered postbiotic, and at least one bacteriocin and/or endolysin, wherein said at least one postbiotic and said at least one bacteriocin and/or endolysin have a synergistic effect in the cosmetic caring of sensitive, sensitized, fragile and/or weakened skin and/or mucosa. In a particular embodiment, said at least one postbiotic, in particular engineered postbiotic, is obtained from microorganisms, in particular bacteria, heterologously expressing said at least one bacteriocin and/or endolysin. In other words, in that embodiment, said at least one bacteriocin and/or endolysin included in said postbiotic composition is part of said postbiotic. In a particular embodiment, said postbiotic, in particular engineered postbiotic, comprises at least one microbial, in particular bacterial, lysate, preferably obtained from microorganisms, in particular bacteria, heterologously expressing said at least one bacteriocin and/or endolysin; and said at least one microbial, in particular bacterial, lysate and said at least one bacteriocin and/or endolysin have a synergistic effect in the cosmetic caring of sensitive, sensitized, fragile and/or weakened skin and/or mucosa. In other words, in the embodiment wherein the engineered postbiotic comprises at least one microbial lysate obtained from microorganisms heterologously expressing said at least one bacteriocin and/or endolysin, said at least one bacteriocin and/or endolysin included in said postbiotic composition is part of said microbial lysate.

The present invention also concerns a method for the cosmetic caring of unaesthetic and/or unpleasant and/or uncomfortable manifestations of sensitive, sensitized, fragile and/or weakened skin and/or mucosa, said skin and/or mucosa being healthy skin and/or mucosa, comprising applying a postbiotic composition comprising at least one postbiotic, in particular at least one engineered postbiotic, and at least one bacteriocin and/or endolysin, wherein said at least one postbiotic and said at least one bacteriocin and/or endolysin have a synergistic effect in the cosmetic caring of unaesthetic and/or unpleasant and/or uncomfortable manifestations of sensitive, sensitized, fragile and/or weakened skin and/or mucosa. In a particular embodiment, said at least one postbiotic, in particular engineered postbiotic, is obtained from microorganisms, in particular bacteria, heterologously expressing said at least one bacteriocin and/or endolysin. In other words, in that embodiment, said at least one bacteriocin and/or endolysin included in said postbiotic composition is part of said postbiotic. In a particular embodiment, said at least one postbiotic, in particular engineered postbiotic, comprises at least one microbial, in particular bacterial, lysate, preferably obtained from microorganisms, in particular bacteria, heterologously expressing said at least one bacteriocin and/or endolysin; and said at least one microbial, in particular bacterial, lysate and said at least one bacteriocin and/or endolysin have a synergistic effect in the cosmetic caring of unaesthetic and/or unpleasant and/or uncomfortable manifestations of sensitive, sensitized, fragile and/or weakened skin and/or mucosa. In other words, in the embodiment wherein the engineered postbiotic comprises at least one microbial lysate obtained from microorganisms heterologously expressing said at least one bacteriocin and/or endolysin, said at least one bacteriocin and/or endolysin included in said postbiotic composition is part of said microbial lysate.

The present invention also concerns a cosmetic method for controlling and/or reducing body odor, comprising applying a postbiotic composition comprising at least one postbiotic, in particular at least one engineered postbiotic, and at least one bacteriocin and/or endolysin, wherein said at least one postbiotic and said at least one bacteriocin and/or endolysin have a synergistic effect in the control and/or reduction of body odor. In a particular embodiment, said at least one postbiotic, in particular engineered postbiotic, is obtained from microorganisms, in particular bacteria, heterologously expressing said at least one bacteriocin and/or endolysin. In other words, in that embodiment, said at least one bacteriocin and/or endolysin included in said postbiotic composition is part of said postbiotic. In a particular embodiment, said at least one postbiotic, in particular engineered postbiotic, comprises at least one microbial, in particular bacterial, lysate, preferably obtained from microorganisms, in particular bacteria, heterologously expressing said at least one bacteriocin and/or endolysin; and said at least one microbial, in particular bacterial, lysate and said at least one bacteriocin and/or endolysin have a synergistic effect in the control and/or reduction of body odor. In other words, in the embodiment wherein the engineered postbiotic comprises at least one microbial lysate obtained from microorganisms heterologously expressing said at least one bacteriocin and/or endolysin, said at least one bacteriocin and/or endolysin included in said postbiotic composition is part of said microbial lysate.

The present invention also concerns a cosmetic method for preventing, reducing and/or eliminating dandruffs, comprising applying a postbiotic composition comprising at least one postbiotic, in particular at least one engineered postbiotic, and at least one bacteriocin and/or endolysin, wherein said at least one postbiotic and said at least one bacteriocin and/or endolysin have a synergistic effect in the prevention, reduction and/or elimination of dandruffs. In a particular embodiment, said at least one postbiotic, in particular engineered postbiotic, is obtained from microorganisms, in particular bacteria, heterologously expressing said at least one bacteriocin and/or endolysin. In other words, in that embodiment, said at least one bacteriocin and/or endolysin included in said postbiotic composition is part of said postbiotic. In a particular embodiment, said at least one postbiotic, in particular engineered postbiotic, comprises at least one microbial, in particular bacterial, lysate, preferably obtained from microorganisms, in particular bacteria, heterologously expressing said at least one bacteriocin and/or endolysin; and said at least one microbial, in particular bacterial, lysate and said at least one bacteriocin and/or endolysin have a synergistic effect in the prevention, reduction and/or elimination of dandruffs. In other words, in the embodiment wherein the engineered postbiotic comprises at least one microbial lysate obtained from microorganisms heterologously expressing said at least one bacteriocin and/or endolysin, said at least one bacteriocin and/or endolysin included in said postbiotic composition is part of said microbial lysate.

Another object of the invention concerns the use, as a cosmetically active ingredient, of a postbiotic composition comprising at least one postbiotic, in particular engineered postbiotic, and at least one bacteriocin and/or endolysin. In a particular embodiment, said at least one postbiotic, in particular engineered postbiotic, is obtained from microorganisms, in particular bacteria, heterologously expressing said at least one bacteriocin and/or endolysin. In other words, in that embodiment, said at least one bacteriocin and/or endolysin included in said postbiotic composition is part of said postbiotic. In a particular embodiment, said at least one postbiotic, in particular engineered postbiotic, comprises a microbial, in particular bacterial, lysate preferably obtained from microorganisms, in particular bacteria, heterologously expressing said at least one bacteriocin and/or endolysin. In other words, in the embodiment wherein the engineered postbiotic comprises at least one microbial lysate obtained from microorganisms heterologously expressing said at least one bacteriocin and/or endolysin, said at least one bacteriocin and/or endolysin included in said postbiotic composition is part of said microbial lysate.

The present invention also relates to a formulation, in particular a cosmetic care formulation, for topical application comprising (i) a postbiotic composition comprising at least one postbiotic, in particular at least one engineered postbiotic, and at least one bacteriocin and/or endolysin, (ii) at least one cosmetically acceptable excipient and/or adjuvant selected from the group consisting of fatty substances, thickeners, emulsifiers, colorants, preservatives, perfumes and combinations thereof, and (iii) optionally an additional active ingredient for the cosmetic care of the skin and/or mucosa.

In a particular embodiment, said at least one postbiotic, in particular engineered postbiotic, obtained from microorganisms, in particular bacteria, heterologously expressing said at least one bacteriocin and/or endolysin. In other words, in that embodiment, said at least one bacteriocin and/or endolysin included in said postbiotic composition is part of said postbiotic. In a particular embodiment, said at least one postbiotic, in particular engineered postbiotic, comprises a microbial, in particular bacterial, lysate, preferably obtained from microorganisms, in particular bacteria, heterologously expressing said at least one bacteriocin and/or endolysin. In other words, in the embodiment wherein the engineered postbiotic comprises at least one microbial lysate obtained from microorganisms heterologously expressing said at least one bacteriocin and/or endolysin, said at least one bacteriocin and/or endolysin included in said postbiotic composition is part of said microbial lysate. In a particular embodiment, said postbiotic is obtained from *Lactobacillus rhamnosus*, in particular from *Lactobacillus rhamnosus* GG, bacteria heterologously expressing lysostaphin. In a particular embodiment, said posbiotic comprises a bacterial lysate obtained from *Lactobacillus rhamnosus*, in particular *Lactobacillus rhamnosus* GG, bacteria heterologously expressing lysostaphin.

DETAILED DESCRIPTION

Engineered Postbiotic

In the context of the invention, a postbiotic composition comprising at least one postbiotic, in particular engineered postbiotic, and at least one bacteriocin and/or endolysin is used.

By "postbiotic" is meant herein non-viable microbial products or metabolic byproducts from probiotic microorganisms that have biologic activity in the subject, or inactivated or killed probiotic microorganisms that have biologic activity in the subject such as *Bifidobacterium longum* 35624, *Lactobacillus acidophilus* CL1285, *Lactobacillus casei* LBC8OR, *Lactobacillus rhamnosus* CLR2, *Lactobacillus reuteri* DSM 17938, *Escherichia coli* Nissle 1917, *Lactobacillus reuteri* ATCC PTA 5289, *Lactobacillus rhamnosus* GG (such as *Lactobacillus rhamnosus* GG LrOs11721 deposited under the Budapest Treaty on Mar. 16, 2022 before CNCM (Collection Nationale de Cultures de Microorganismes, Institut Pasteur, 25 rue du Docteur Roux, 75724 Paris, France) under deposit number CNCM 1-5833, or *Lactobacillus rhamnosus* GG ATCC 53103), *Lactobacillus rhamnosus* GR-1, *Lactobacillus reuteri* RC-14, *Lactobacillus crispatus* LbV 88, *Lactobacillus jensenii* LbV 116, *Lactobacillus gasseri* LbV 150N, *Lactobacillus rhamnosus* LbV 96, *Lactobacillus plantarum* NCIMB 1193 or *Bifidobacterium animalis* subsp. *lactis* Bb12.

In a preferred embodiment, said postbiotic is an engineered postbiotic, i.e. a postbiotic obtained from an engineered probiotic microorganism.

The postbiotic composition, used in the context of the invention comprises at least one postbiotic, in particular an engineered postbiotic, and at least one bacteriocin and/or endolysin, in particular at least two, at least three, at least four, at least five or at least ten bacteriocins and/or endolysins. In a particular embodiment, the postbiotic composition used in the context of the invention comprises at least one postbiotic, in particular engineered postbiotic, and at least two bacteriocin and/or endolysin.

By "bacteriocin" is meant herein a proteinaceous or peptidic toxin produced by bacteria to inhibit the growth of similar or closely related bacterial strain(s).

Bacteriocins are categorized in several ways, including producing strain, common resistance mechanisms, and mechanism of killing. Such bacteriocins have been described from gram negative bacteria (e.g. microcins, colicin-like bacteriocins and tailocins) and from gram positive bacteria (e.g. Class I, Class II, Class III or Class IV bacteriocins).

In one embodiment, said at least one bacteriocin is selected from the group consisting of microcins, colicin-like bacteriocins, tailocins, Class I, Class II, Class III and Class IV bacteriocins.

By "microcins" is meant herein very small bacteriocins, composed of relatively few amino acids, and typically including microcin V (MccV) produced by *Escherichia coli* and subtilosin A produced by *Bacillus subtilis*. Examples of microcins include MccB17, MccC, MccD93, MccJ25, MccL, MccV, MccS, MccE492, MccM, MccH47, Mccl47, MccN and MccPDI.

By "colicin-like bacteriocin" or "CLBs" is meant herein bacteriocins found in Gram-negative bacteria, which are modular proteins between 20 and 90 kDa in size and often consist of a receptor binding domain, a translocation domain and a cytotoxic domain. Examples of CLBs typically include colicins, in particular colicins A, B, D, K, E1, E2, E3, E4, E5, E6, E7, E8, E9, Ia, Ib, M, N, S4, U, Y, 5, 10; klebicins, in particular klebicins A, B, C, CCL, D, KpneA, KaerA, KoxyY, Kvarla, Kpnela, KaerM, KpneM (or Kpne CHS110), KpneM2 (or Kpne e1602) and KvarM (or Kvar 6A2); alveicins, in particular alveicins A and B; marcescins, in particular marcescins A, B and 28B; S-type pyocins, in particular pyocins S1, S2, S3, S5, S4, AP41; cloacins, in particular cloacin DF13; and pesticin.

By "tailocin" is meant herein a multisubunit bacteriocin that resembles bacteriophage tails. There are two classes of tailocin particles, the flexible noncontractile F-tailocins and the rigid contractile R-tailocins, which resemble and are evolutionarily related to Siphoviridae and Myoviridae phage tails, respectively. Examples of tailocins typically include F-type and R-type pyocins, carotovoricin, xenorhabdicin, and maltocin.

As used herein, the term "Class I bacteriocin" refers to small peptide inhibitors which include nisin and other lantibiotics. Examples of Class I bacteriocins typically include type A lantibiotics such as nisin A, nisin Z, bisin, subtilin, epidermin, gallidermin, mutacin II, mutacin I, mutacin III, pep5, epicidin 280, epilancin K7, lacticin 481, lacticin 3147, cytolysin, staphylococcin C55, salvaricin A, lactocin S, streptococcin A-FF2, sublancin 168, carnocin U149, variacin 8 and cypemycin; and type B lantibiotics such as mersacidin, actagardine, duramycin B, duramycin C, cinnamycin, ancovenin, and plantaricin C.

As used herein, the term "Class II bacteriocin" refers to small (<10 kDa) heat-stable bacteriocins, subdivided into five subclasses: the class IIa bacteriocins (pediocin-like bacteriocins), which correspond to the largest subgroup and contain an N-terminal consensus sequence across this group and a C-terminal region responsible for species-specific activity, causing cell-leakage by permeabilizing the target cell wall; the class IIb bacteriocins (two-peptide bacteriocins) which require two different peptides for activity; the class IIc bacteriocins which encompass cyclic peptides, in which the N-terminal and C-terminal regions are covalently linked; the class IId bacteriocins which cover single-peptide bacteriocins, which are not post-translationally modified and do not show the pediocin-like signature; and the class IIe bacteriocins, which encompass those bacteriocins composed of three or four non-pediocin like peptides. Examples of class IIa bacteriocins typically include pediocin, pediocin A, pediocin AcH, pediocin PA-1, pediocin PP-1, pediocin SJ-1, prepediocin AcH, prepediocin PA-1, mesentericin Y105, mesentericin 52A, carnobacteriocin B2, carnobacteriocin BM1, sakacin A, sakacin G, sakacin P, sakacin X, enterocin A, enterocin BC25, enterocin P, enterocin P-like, enterocin CRL35, enterocin HF, enterocin SE-K4, leucocin A, leucocin B-Ta11a, leucocin C, leucocin C-TA33a, curvacin A, listeriocin 743A, avicin A, bavaricin A/SppA, curvaticin L442, mundticin, mundticin CRL35, mundticin KS, mundticin L, mundticin QU2, pediocin ACCEL, piscicocin CS526, piscicolin 126, piscicolin 126, piscicocin V1a, bifidocin B, CoaA/Coagulin/CoaA, mutacin F-59.1, PapA, weissellin A, bacteriocin 602, bavaricin MN, divercin V41, divergicin M35, duracin GL, bacteriocin 31/BacA, bacteriocin 1580, bacteriocin 43, bacteriocin RC714, bacteriocin T8, hiracin JM79, penocin A/PenA, bacteriocin MC4-1, carnocin CP52, plantaricin 423, plantaricin C19, prebacteriocin SkgA2, lactococcin MMFII, ubericin A, piscicocin V1b, bacteriocin E50-52, bacteriocin L-1077, bacteriocin 37, acidocin A, and bacteriocin OR-7. Examples of class IIb bacteriocins typically include enterocin C, enterocin 1071, gassericin T, gassericin S, lactococcin G, lactococcin Q, plantaricin E/F, plantaricin J/K, plantaricin S, plantaricin NC8, lactacin F, brochocin-C, thermophilin 13, ABP-118, salivaricin P, mutacin IV and lactocin 705. Examples of class IIc bacteriocins typically include enterocin AS-48, lactocyclicin Q, garvicin ML, gassericin A, acidocin B and butyrovibriocin AR10. Examples of class IId bacteriocins typically include aureocin A53, garvicin A, laterosporulin10, lactococcin A, lactococcin 972, lacticin Q, carnobacteriocin XY, leucocin B, thuricin S, thuricin-17 and bactofensin A. Examples of class IIe bacteriocins typically include aureocin A70.

As used herein, the term "Class III bacteriocin" refers to large (>10 kDa), heat-labile protein bacteriocins. This class is subdivided in two subclasses: subclass IIIa (bacteriolysins) and subclass IIIb. Subclass IIIa comprises those peptides that kill bacterial cells by cell wall degradation, thus causing cell lysis, and typically include Lysostaphin. Subclass IIIb, in contrast, comprises those peptides that do not cause cell lysis, killing the target cells by disrupting plasma membrane potential. Examples of class III bacteriocins typically include Lysostaphin, enterolysin A, helveticin V-1829, helveticin J, caseicin 80, lactacin A, lactacin B, zoocin A, millericin B, linocin M18 and acidophilus A.

As used herein, the term "Class IV bacteriocin" refers to complex bacteriocins containing lipid or carbohydrate moieties. Examples of class IV bacteriocins typically include sublancin 168, glycocin F, ASM1, enterocin 96 and enterocin F4-9.

In a particular embodiment, said at least one bacteriocin and/or endolysin is a bacteriocin as defined above, more particularly a Class III bacteriocin as defined above, more particularly Lysostaphin.

By "Lysostaphin" is meant herein a *Staphylococcus simulans* metalloendopeptidase, typically of sequence SEQ ID NO: 1, which specifically targets *Staphylococcus aureus*. In the context of the invention, the term "Lysostaphin" further encompasses any modified lysostaphin or variant of lysostaphin. In a particular embodiment, said lysostaphin comprises or consists of an amino acid sequence at least 80% identical, preferably at least 85%, at least 90%, at least 95% or at least 99% identical to the sequence SEQ ID NO: 1.

As used herein, the percent identity is calculated in relation to polymers (e.g., polynucleotide or polypeptide) whose sequences have been aligned. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4: 11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available at www.gcg.com), using a BLOSUM62 matrix, a BLOSUM30 matrix or a PAM250 matrix, and a gap weight of 16, 14, 12, 10, 8, 6, or 4 and a length weight of 1, 2, 3, 4, 5, or 6. In a specific embodiment the BLOSUM30 matrix is used with gap open penalty of 12 and gap extension penalty of 4.

By "endolysin" or "lysin" is meant herein enzymes used by bacteriophages at the end of their replication cycle to degrade the peptidoglycan of the bacterial host from within, resulting in cell lysis and release of progeny virions. They are typically either β(1,4)-glycosylases (lysozymes), transglycosylases, amidases or endopeptidases. Examples of endolysins typically include PhiV10p30, STM0907.Fels0, epsilon15p25, YuA20, ORF23, BcepMu22, F116p62, STM2715.S.Fels2, gp76, SPSV3_gp23, phi32_17, HK022p54, HK97p58, HK620p36, VIP0007, Sf6p62, R (SfVp40), gp22, Nazgul38, K (P2p09), K (Wphi09), rv5_gp085, EpJS98_gp116, gp3.5 (from 13A phage), gp3.5 (from BA14 phage), gp3.5 (from ECODS1 phage), CKV1F_gp16, T3p18, gh-1p12, gp3.5 (from K11 phage), ORF12, Bcep43-27, Bcep781-27, Bcep1-28, BcepNY3gene26, gp45, gp28, P27p30, RB49p102, philp102, lys (T5.040), Aeh1p339, YYZgp45, φSH2 lysin, lysin from STB12 phage, PlyP40, endolysin from phi11 phage, endolysins from the *Pseudomonas aeruginosa* phages DKZ and EL, endolysins of the Pseudomonas putida phage, endolysins of the *E. coli* phage N4, endolysins of the phage LUZ24, gp61 muramidase, STM0016 endolysin, PSP3 endolysin, phiKZgp144, ELgp188, Salmonella endolysin, Enterobacteria phage T4 endolysin, *Acinetobacter baumanii* endolysin, *E. coli* phage KIF endolysin, OBPgpLYS, PSP3 Salmonella endolysin (PSP3gp1), *E. coli* phage P2 endolysin (P2gp9), *Salmonella typhimurium* phage muramidase STMOO16, *E. coli* phage N4 muramidase N4-gp61 and KZ144. Examples of endolysins also include endolysins disclosed in Fernández-Ruiz et al. (2018) *Front. Microbiol.* 9:1033.

In a particular embodiment, the endolysin is encoded by bacteriophages specific for Gram-negative bacteria such as Enterobacteriaceae (*Escherichia*, especially *E. coli*, *Salmonella*, *Shigella*, *Citrobacter*, *Edwardsiella*, *Enterobacter*, *Hafnia*, *Klebsiella*, especially *K. pneumoniae*, *Morganella*, *Proteus*, *Providencia*, *Serratia*, *Yersinia*), Pseudomonadaceae (*Pseudomonas*, especially *P. aeruginosa*, *Burkholderia*, *Stenotrophomonas*, *Shewanella*, *Sphingomonas*, *Comamonas*), *Neisseria*, *Moraxella*, *Vibrio*, *Aeromonas*, *Brucella*, *Francisella*, *Bordetella*, *Legionella*, *Bartonella*, *Coxiella*, *Haemophilus*, *Pasteurella*, *Mannheimia*, *Actinobacillus*, *Gardnerella*, Spirochaetaceae (*Treponema* and *Borrelia*), Leptospiraceae, *Campylobacter*, *Helicobacter*, *Spirillum*, *Streptobacillus*, Bacteroidaceae (*Bacteroides*, *Fusobacterium*, *Prevotella*, *Porphyromonas*), *Acinetobacter*, especially *A. baumanii*.

In the context of the invention, said at least one bacteriocin and/or endolysin may be a wild-type bacteriocin and/or endolysin or an engineered bacteriocin and/or endolysin, in particular a bacteriocin and/or endolysin mutant, variant or chimera, typically comprising modifications and/or alterations of the amino acid sequence. Such alterations and/or modifications may comprise mutations such as deletions, insertions and additions, substitutions or combinations thereof and/or chemical changes of the amino acid residues, e.g. biotinylation, acetylation, pegylation, chemical changes of the amino-, SH- or carboxyl-groups. Such modified bacteriocin and/or endolysin typically exhibit the lytic activity of the respective wild-type bacteriocin and/or endolysin. However, said activity can be the same, higher or lower than the activity of the respective wild-type bacteriocin and/or endolysin. Said activity can be about 10, 20, 30, 40, 50, 60, 70, 80, 90, 100, 110, 120, 130, 140, 150, 160, 170, 180, 190 or about 200% of the activity of the respective wild-type bacteriocin and/or endolysin or even more. The activity can be measured by assays well known in the art by a person skilled in the art as e.g. the plate lysis assay or the liquid lysis assay which are e.g. described in Briers et al. (2007) *J. Biochem. Biophys Methods* 70:531-533, or Donovan et al. (2006) *FEMS Microbiol Lett.* 265:133-139.

In a particular embodiment, said at least one bacteriocin and/or endolysin targets at least one commensal bacterial species of the subject.

By "commensal bacterial species of a subject" is meant herein bacteria commonly associated with a healthy state of a microbiome in a particular niche, e.g., the gastrointestinal tract or the skin, and/or are generally considered non-pathogenic.

Commensal bacterial species in a particular niche of a subject are well-known from the skilled person.

Skin commensal bacteria are typically bacteria of the Actinobacteria phylum in particular of the Corynebacteriaceae family, the Propionibacteriaceae family and the Micrococcaceae family; of the Firmicutes phylum, in particular of Staphylococaceae family, of Lactobacillales order and of Clostridiales order; or of the Proteobacteria phylum. Examples of skin commensal bacteria typically include those of the genus *Staphylococcus, Cutibacterium, Corynebacterium, Streptococcus, Micrococcus, Bacillus, Brevibacterium, Kocuria, Roseomonas, Paenibacillus, Acinetobacter, Dietza, Dermacoccus, Enhydrobacter, Pseudomonas, Paracoccus, Microbacterium, Sporosarcina, Brachybacterium, Lysinibacillus, Aerococcus, Brevundimonas, Okibacterium, Pantoea, Variovorax* most precisely *Staphylococcus epidermidis, Staphylococcus hominis, Staphylococcus capitis, Staphylococcus wameri, Staphylococcus haemolyticus, Cutibacterium acnes* (formerly called *Propionibacterium acnes*), *Cutibacterium avidum, Cutibacterium granulosum, Corynebacterium tube rculostearicum, Corynebacterium afermentans, Corynebacterium simulans, Corynebacterium resistens, Corynebacterium kroppenstedtii, Corynebacterium aurimucosum, Corynebacterium amycolatum, Streptococcus mitis, Streptococcus oralis, Streptococcus pseudo pneumoniae, Streptococcus sanguinis, Micrococcus luteus, Bacillus cereus, Bacillus subtilis, Brevibacterium epidermidis, Veillonella parvula, Enhydrobacter aerosaccus.*

In an alternative embodiment, said at least one bacteriocin and/or endolysin targets at least one unfavorable bacterial species.

By "unfavorable bacterial species" is meant herein bacterial species which can be or become responsible for esthetic disorders in a subject, such as the unaesthetic and/or unpleasant and/or uncomfortable manifestations of sensitive, sensitized, fragile and/or weakened skin and/or mucosa, or body odors.

By "targeting a particular species" is meant herein that said bacteriocin and/or endolysin is able to recognize, preferably specifically recognize, a particular species, and to exert, preferably specifically exert, their bactericidal, bacteriostatic and/or lytic activity on said particular species.

By "specifically targets a particular species" is meant herein that said bacteriocin and/or endolysin bind to and/or exert their activity on said particular species but does not significantly bind to other species, and/or do not exert their activity on other species, in particular on commensal bacterial species, in a significant way, in particular to an extent which affects the use of said postbiotic, in particular engineered postbiotic, in cosmetic applications.

In a particular embodiment, said bacteriocin and/or endolysin specifically targets at least one unfavorable bacterial species, in particular by exerting its killing activity on said at least one unfavorable bacterial species, without killing commensal bacterial species. In a more particular embodiment, said bacteriocin and/or endolysin has a killing/reduction activity level on said at least one unfavorable bacterial species, at least 1 log, at least 2 log, at least 3 log or at least 4 log higher than on commensal bacterial species.

In a particular embodiment, the postbiotic composition of the invention comprises at least two, in particular at least three, at least four, at least five, or more different bacteriocins and/or endolysins. In particular, the postbiotic composition of the invention may comprise at least one bacteriocin and at least one endolysin. Alternatively, the postbiotic composition of the invention may comprise at least two bacteriocins. Alternatively, the postbiotic composition of the invention may comprise at least two endolysins. In a particular embodiment, the postbiotic composition of the invention comprises lysostaphin, and at least one other bacteriocin and/or endolysin.

In the embodiment wherein the postbiotic composition of the invention comprises at least two different bacteriocins and/or endolysins, said at least two different bacteriocins and/or endolysins may target the same bacterial species, in particular may target the same commensal or the same unfavorable bacterial species. Alternatively, in said embodiment, said at least two different bacteriocins and/or endolysins may target different bacterial species, in particular different commensal bacterial species, or different unfavorable bacterial species, or both commensal and unfavorable bacterial species.

In an embodiment of the invention, said at least one bacteriocin and/or endolysin is heterologously expressed by the microorganism, in particular by the bacteria, from which at least one postbiotic, in particular at least one engineered postbiotic, is obtained. Accordingly, in a particular embodiment, said at least one bacteriocin and/or endolysin is comprised in said at least one postbiotic, in particular in said at least one engineered postbiotic.

In a more particular embodiment of the invention, said at least one bacteriocin and/or endolysin is heterologously expressed by the microorganism, in particular by the bacteria, from which the at least one microbial, in particular bacterial, lysate, comprised in said at least one engineered postbiotic, is obtained. Accordingly, in a particular embodiment, said at least one bacteriocin and/or endolysin is comprised in said at least one microbial, in particular bacterial, lysate, comprised in said at least one engineered postbiotic.

As used herein, the term "heterologous" means derived from a different species or derived from a different organism.

The term "heterologous expression" means transcription and optionally translation of nucleotide sequences which are not native to the cell but which have been incorporated into the cell's chromosomal or extra-chromosomal expression system, or as extra-chromosomal expression system, by genetic engineering techniques known in the art.

In a particular embodiment, said at least one bacteriocin and/or endolysin is not secreted by said microorganism, in particular said bacteria. Accordingly, in a particular embodiment, said at least one bacteriocin and/or endolysin is not present in the cell culture supernatant of said microorganism, in particular of said bacteria. In an alternative embodiment, said at least one bacteriocin and/or endolysin is secreted by said microorganisms, in particular said bacteria.

In a particular embodiment, said microorganism, in particular bacteria, in particular heterologously expressing said at least one bacteriocin and/or endolysin, is GRAS and/or probiotic microorganism, in particular bacteria.

By "GRAS microorganism" or "Generally Recognized as Safe microorganism" is meant herein microorganisms considered as safe by the FDA when used as food ingredients. Examples of GRAS microorganisms typically include *Bacillus cereus, Bacillus coagulans, Bacillus lentus, Bacillus lincheniformis, Bacillus pumilus, Bacillus subtilis, Bacteroides amylophilus, Bacteroides capillosus, Bacteroides ruminocola, Bacteroides suis, Bifidobacterium adolescentis, Bifidobacterium animalis, Bifidobacterium bifidum, Bifidobacterium breve, Bifidobacterium infantis, Bifidobacterium lactis, Bifidobacterium longum, Bifidobacterium thermophilum, Escherichia coli* Nissle 1917, *Lactobacillus acidophilus, Lactobacillus brevis* (also called *Levilactobacillus brevis*), *Lactobacillus bulgaricus* (also called *Lactobacillus delbrueckii* subsp. *bulgaricus*), *Lactobacillus casei* (also called *Lacticaseibacillus casei*), *Lactobacillus cellobiosus, Lactobacillus curvatus* (also called *Latilactobacillus curvatus*), *Lactobacillus delbruekii, Lactobacillus fermentum* (also called *Limosilactobacillus fermentum*), *Lactobacillus gasseri, Lactobacillus johnsonii, Lactobacillus paracasei* (also called *Lacticaseibacillus paracasei*), *Lactobacillus plantarum* (also called *Lactiplantibacillus plantarum*), *Lactobacillus reuteri* (also called *Limosilactobacillus reuteri*), *Lactobacillus salivarius* (also called *Ligilactobacillus salivarius*), *Lactococcus lactis, Leuconostoc mesenteroides, Pediococcus acidilacticii, Pediococcus cerevisiae, Pediococcus pentosaceus, Propionibacterium freudenreichii, Propionibacterium shermanii, Streptococcus cremoris, Streptococcus diacetylactis, Streptococcus faecium, Streptococcus intermedius, Streptococcus lactis* and *Streptococcus thermophilus, Saccharomyces boulardii* and *Saccharomyces cerevisiae.*

As used herein, "probiotic microorganisms" refer to living microorganisms which, when taken in adequate quantities, have a beneficial effect on the host organism. Probiotic microorganisms can comprise a non-pathogenic microbial population. Probiotics include, but are not limited to lactobacilli, bifidobacteria, streptococci, enterococci, propionibacteria, saccharomycetes, proteobacteria, or saccharomyces. Examples of probiotic bacteria include, without limitation, strains of *Lactobacillus acidophilus, Lactobacillus casei* (also called *Lacticaseibacillus casei*), *Lactobacillus paracasei* (also called *Lacticaseibacillus paracasei*), *Lactobacillus rhamnosus* (also called *Lacticaseibacillus rhamnosus*), in particular *Lactobacillus rhamnosus* GG (such as *Lactobacillus rhamnosus* GG LrOs11721 deposited under the Budapest Treaty on Mar. 16, 2022 before CNCM (Collection Nationale de Cultures de Microorganismes, Institut Pasteur, 25 rue du Docteur Roux, 75724 Paris, France) under deposit number CNCM I-5833, or *Lactobacillus rhamnosus* GG ATCC 53103), *Lactobacillus delbrueckii* subsp. *bulgaricus, Lactobacillus brevis* (also called *Levilactobacillus brevis*), *Lactobacillus johnsonii, Lactobacillus plantarum* (also called *Lactiplantibacillus plantarum*), *Lactobacillus fermentum* (also called *Limosilactobacillus fermentum*), *Lactobacillus reuteri* (also called *Limosilactobacillus reuteri*), *Bifidobacterium lactis* (in particular *Bifidobacterium lactis* DN-173 010), *Bifidobacterium animalis* subsp. *lactis, Bifidobacterium infantis, Bifidobacterium adolescentis, Bifidobacterium animalis* subsp *animalis, Bifidobacterium animalis* subsp *lactis, Bifidobacterium bifidum, Bifidobacterium longum, Bifidobacterium breve, Lactococcus lactis* subsp. *lactis, Enterococcus durans, Enterococcus faecium, Streptococcus thermophilus, Bacillus subtilis, Bacillus coagulans, Bacillus cereus, Pediococcus acidilactici, Leuconostoc mesenteroides* and *Escherichia coli*, in particular *E. coli* Nissle 1917. Examples of probiotic strains include *B. longum* 35624, *L. acidophilus* CL1285, *L. casei* LBC80R, *L. rhamnosus* CLR2, *L. reuteri* DSM 17938, *Escherichia coli* Nissle 1917, *L. reuteri* ATCC PTA 5289, *L. rhamnosus* GG (such as *L. rhamnosus* GG LrOs11721 deposited under the Budapest Treaty on Mar. 16, 2022 before CNCM (Collection Nationale de Cultures de Microorganismes, Institut Pasteur, 25 rue du Docteur Roux, 75724 Paris, France) under deposit number CNCM I-5833, or *L. rhamnosus* GG ATCC 53103), *L. rhamnosus* GR-1, *L. reuteri* RC-14, *L. crispatus* LbV 88, *L. jensenii* LbV 116, *L. gasseri* LbV 150N, *L. rhamnosus* LbV 96, *Lactobacillus plantarum* NCIMB 1193, *B. lactis* Bb12. Examples of probiotic yeasts include *Saccharomyces boulardii* and *Saccharomyces cerevisiae.*

In a particular embodiment, said bacteria, in particular heterologously expressing said at least one bacteriocin and/or endolysin, as defined above, are *Lactobacillus* or *Escherichia* bacteria, more particularly bacteria selected from the group consisting of *Lactobacillus rhamnosus, Lactobacillus plantarum* and *Escherichia coli* bacteria.

In a particular embodiment, said bacteria, in particular heterologously expressing said at least one bacteriocin and/or endolysin, as defined above, are *Lactobacillus rhamnosus* bacteria, more particularly *Lactobacillus rhamnosus* GG bacteria (such as *Lactobacillus rhamnosus* GG LrOs11721 deposited under the Budapest Treaty on Mar. 16, 2022 before CNCM (Collection Nationale de Cultures de Microorganismes, Institut Pasteur, 25 rue du Docteur Roux, 75724 Paris, France) under deposit number CNCM 1-5833, or *Lactobacillus rhamnosus* GG ATCC 53103).

In a particular embodiment, said microorganisms, in particular bacteria, more particularly heterologously expressing said at least one bacteriocin and/or endolysin, as defined above, are obtained from microorganisms, in particular bacteria, isolated from a subject In particular, said microorganisms, in particular bacteria, may be obtained from a subject's skin or gut microbiota, more particularly from a subject's skin microbiota. In a particular embodiment, said subject is of the same species as the subject on whom the cosmetic care method of the invention is applied, more particularly said subject is the subject on whom the cosmetic care method of the invention is applied.

In the context of the invention, said microorganisms, in particular bacteria, heterologously expressing said at least one bacteriocin and/or endolysin, as defined above, have typically been genetically modified to express said at least one bacteriocin and/or endolysin.

In a particular embodiment, when said microorganisms have been genetically modified to express said at least one bacteriocin and/or endolysin, the microorganisms from which said genetically modified microorganisms are obtained, are isolated from a subject, in particular from a subject's skin or gut microbiota, more particularly from a subject's skin microbiota. In a particular embodiment, said subject is of the same species as the subject on whom the cosmetic care method of the invention is applied, more particularly said subject is the subject on whom the cosmetic care method of the invention is applied.

Said microorganisms, in particular bacteria, can be genetically modified to express said at least one bacteriocin and/or endolysin by any suitable technique, well-known from the skilled person. For example, said bacteria can be genetically modified by transformation (chemical transformation or ultrasound transformation), transduction (using for example optionally engineered bacteriophages, or packaged phagemids technologies), conjugation, or electroporation.

In a particular embodiment, said microorganisms, in particular bacteria, more particularly said microorganisms, in particular bacteria, heterologously expressing said at least one bacteriocin and/or endolysin, as defined above, do not comprise any antibiotic resistance marker. Therefore, other types of selection markers, than antibiotic resistance markers, may be used when genetically modifying said microorganisms, in particular bacteria. For example, suitable selection markers include auxotrophic selection markers such as alr (alanine racemase), thyA (Thymidylate synthase), dapA (4-hydroxy-tetrahydrodipicolinate synthase). In a particular embodiment, said auxotrophic selection marker is alr. In another particular embodiment, said auxotrophic selection marker is thyA.

In a particular embodiment, said microorganisms, in particular bacteria, more particularly said microorganisms, in particular bacteria, heterologously expressing said at least one bacteriocin and/or endolysin, as defined above, do not comprise any antibiotic resistance marker and the bacteriocin expression cassette is integrated in the genome of said microorganisms, in particular bacteria, and no antibiotic resistance marker is present in the engineered microorganisms, in particular bacteria.

In a particular embodiment, the postbiotic, in particular engineered postbiotic, of the invention comprises a microbial, in particular bacterial, lysate, more particularly a bacterial ferment lysate.

As used herein, the term "microbial lysate" refers to the composition obtained after the destruction or dissolution of microbial cells via cell lysis which results in the release of the intracellular biological constituents contained in the microbial cells. Microorganisms, in particular bacteria, lysis may be accomplished via various techniques, such as an osmotic shock, a heat-treatment (e.g., tyndallization), via ultrasonication, via high pressure homogenisation, chemically (e.g., formaldehyde), via irradiation (e.g., gamma or ultraviolet rays) or alternatively under a mechanical stress of centrifugation type. In a particular embodiment, the microbial cell debris is removed prior to use. In more particular embodiments the microbial, in particular bacterial, lysates are filtered prior to use, leading to a bacterial lysate filtrate. In exemplary embodiments, the microbial, in particular bacterial, cells are lysed by, for example bead beating or high pressure homogenisation. In a particularly preferred embodiment, said bacterial lysate is a bacterial ferment lysate filtrate. In a particular embodiment, said microbial, in particular bacterial, lysate is not heat-inactivated.

By "bacterial ferment lysate" is meant herein a bacterial lysate, as defined above, obtained from bacteria after fermentation.

In a particular embodiment, said postbiotic, in particular said engineered postbiotic, acts as a prebiotic and/or has a beneficial effect on commensal microorganisms, in particular commensal bacteria. In a more particular embodiment, said microbial, in particular bacterial, lysate acts as a prebiotic and/or has a beneficial effect on commensal microorganisms, in particular commensal bacteria.

By "prebiotic" is meant herein an ingredient that allows specific changes, both in the composition and/or activity in the subject's microbiota that may confer benefits upon the subject.

In a particular embodiment, said postbiotic, in particular said microbial, more particularly bacterial, lysate stimulates growth of at least one commensal bacterial species, as defined above, of the subject.

In the embodiment wherein said postbiotic, in particular said microbial, more particularly bacterial, lysate, acts as a prebiotic and/or has a beneficial effect on commensal microorganisms, more particularly stimulates growth of at least one commensal bacterial species, as defined above, of the subject, said at least one bacteriocin and/or endolysin, as defined above, may target at least one unfavorable bacterial species, as defined above.

In a particular embodiment, the at least one postbiotic, in particular engineered postbiotic, is constituted by the at least one microbial, in particular bacterial, lysate, as defined above, and the at least one bacteriocin and/or endolysin, as defined above, said at least one bacteriocin and/or endolysin being preferably part of the microbial, in particular bacterial, lysate.

In a particular embodiment, the postbiotic composition comprises a mixture of postbiotics, in particular of engineered postbiotics, preferably a mixture of microbial, in particular bacterial, lysates, as defined above.

In said particular embodiment, the postbiotic composition may comprise (i) a postbiotic, in particular an engineered postbiotic, preferably a microbial, in particular bacterial, lysate, obtained from microorganisms, in particular bacteria, which heterologously express said at least one bacteriocin and/or endolysin, and (ii) at least one other postbiotic, preferably microbial, in particular bacterial, lysate, obtained from microorganisms, in particular bacteria, which do not express any heterologous bacteriocin and/or endolysin, or which heterologously express another bacteriocin and/or endolysin.

In a particular embodiment, the postbiotic composition of the invention comprises a mixture of postbiotic, in particular microbial, in particular bacterial, lysate, as defined above, and of at least one isolated bacteriocin and/or endolysin, as defined above. By "mixture of postbiotic and of at least one isolated bacteriocin and/or endolysin" is meant herein that the at least one bacteriocin and/or endolysin was not expressed by the microorganisms from which the postbiotic is obtained, but was added to said postbiotic.

Cosmetic Caring

The present invention concerns the use, as a cosmetically active ingredient, of a postbiotic composition comprising at least one postbiotic, in particular engineered postbiotic, as defined in the section "Engineered postbiotic" above, and at least one bacteriocin and/or endolysin, as defined in the section "Engineered postbiotic" above. In a particular embodiment, said postbiotic, in particular engineered postbiotic, is obtained from microorganisms, in particular bacteria, heterologously expressing said at least one bacteriocin and/or endolysin, as defined in the section "Engineered postbiotic". In a particular embodiment, said postbiotic, in particular engineered postbiotic, comprises a microbial, in particular bacterial, lysate, as defined in the section "Engineered postbiotic" above, preferably obtained from microorganisms, in particular bacteria, heterologously expressing said at least one bacteriocin and/or endolysin, as defined in the section "Engineered postbiotic".

By "cosmetically active ingredient" is meant herein an ingredient that confers an aesthetic feature to the substrate to which it is applied, such as the skin.

The present invention also relates to a method for the cosmetic caring of the skin and/or mucosa of a subject, comprising applying a postbiotic composition comprising at least one postbiotic, in particular engineered postbiotic, as defined in the section "Engineered postbiotic" above, and at least one bacteriocin and/or endolysin, as defined in the section "Engineered postbiotic" above, wherein said at least one postbiotic and said at least one bacteriocin and/or endolysin have a synergistic effect in the cosmetic caring method.

In a particular embodiment, said postbiotic, in particular engineered postbiotic, is obtained from microorganisms, in particular bacteria, heterologously expressing said at least one bacteriocin and/or endolysin, as defined in the section "Engineered postbiotic" above. In a particular embodiment, said postbiotic, in particular engineered postbiotic, comprises a microbial, in particular bacterial, lysate, as defined in the section "Engineered postbiotic" above, preferably obtained from microorganisms, in particular bacteria, heterologously expressing said at least one bacteriocin and/or endolysin, as defined in the section "Engineered postbiotic" above, and wherein said microbial, in particular bacterial, lysate and said at least one bacteriocin and/or endolysin preferably have a synergistic effect in the cosmetic caring method.

By "cosmetic caring of the skin and/or mucosa" is meant herein a cosmetic non-therapeutic care that addresses normal, healthy skin and/or mucosa, said care being intended to improve its appearance and condition. Such care has no therapeutic aim.

According to one embodiment of the present invention, the skin refers to the skin of the arms, especially the hands, the skin of the legs, especially the feet, the skin of the armpits, the skin of the neck, the skin of the chest, the skin of the back, the skin of the scalp, and/or the skin of the face, preferably the skin of the face.

As used herein, the term "mucosa" refers to a membrane that lines various cavities in the body or covers those surfaces. It is continuous with the skin at various body openings such as the eyes, ears, inside the nose, inside the mouth, lip, vagina, the urethral opening and the anus. Some mucous membranes secrete mucus. Mucosa typically include, e.g., oral mucosa, tongue, vaginal mucosa, nasal mucosa, and the anal canal.

By "synergistic effect" is meant a greater-than-additive effect that is produced by the combination of the postbiotic, preferably the microbial lysate, and of the at least one bacteriocin and/or endolysin (optionally expressed by the microorganisms, in particular bacteria, from which said postbiotic, preferably microbial lysate is obtained) as compared to each of the postbiotic, preferably microbial lysate (obtained from microorganisms, in particular bacteria, which do not express said at least one bacteriocin and/or endolysin) and the at least one bacteriocin and/or endolysin alone. In some embodiments, synergy or synergistic effect refers to an advantageous effect of using the postbiotic, preferably the microbial lysate, and the at least one bacteriocin and/or endolysin (optionally expressed by the microorganisms, in particular bacteria, from which said postbiotic, preferably microbial lysate, is obtained) in combination, e.g., in a cosmetic composition, or in a method of cosmetic care.

In a particular embodiment, said at least one postbiotic and said at least one bacteriocin and/or endolysin has a synergistic effect on killing and/or inhibiting the growth of the bacterial species targeted by said at least one bacteriocin and/or endolysin.

In a particular embodiment, said method of cosmetic care is for the non-therapeutic cosmetic care of sensitive, sensitized, fragile and/or weakened skin and/or mucosa, said skin and/or mucosa being healthy skin and/or mucosa.

By "sensitive skin and/or mucosa" is meant herein a skin and/or mucosa which, by nature, does not tolerate aggressive agents well, especially environmental agents such as pollutants, climate factors (wind, cold, heat), emotional factors, especially stress and/or chemical agents (heavy metals, detergents, compounds contained in cosmetic compositions such as fragrances, preservatives, alcohols, pH, AHA or dermatological treatments, such as vitamin A acid) and/or aggressive conditions, including perspiration and mechanical aggression such as waxing, shaving, rubbing and even water, especially hard water. Sensitive skin is not pathological skin, unlike allergic skin. Nevertheless, it may react to aggressive agents and/or conditions by unaesthetic and/or uncomfortable cutaneous and/or mucosal manifestations such as stinging, feeling of heat or warmth, tension, tingling, tightness and redness. Thus the "sensitive skin" character may be estimated by the subject themselves with subjective cutaneous sensations or by the dermatologist with objective cutaneous reactions.

By "sensitized skin and/or mucosa" is meant herein a skin and/or mucosa momentarily made sensitive, as defined above, therefore nonpathological as such.

By "fragile" and/or "weakened skin and/or mucosa" (i.e. skin and/or mucosa made momentarily fragile), is meant herein a skin and/or mucosa whose barrier function is weakened. This may be linked to the status of the individual; elderly people and infants have more fragile skin, for example. This state may result from chemical or physical aggression (abrasion, rubbing for example).

The uncomfortable and unaesthetic manifestations of sensitized, fragile and/or weakened skin and/or mucosa are the same as for sensitive skin and/or mucosa, without these manifestations and/or skin conditions being considered to involve the prevention and/or treatment of a pathology.

For the purposes of the present invention, "cosmetic" is intended to mean a non-pharmaceutical, non-therapeutic use, which is not intended for prevention and/or treatment of skin and/or mucosa qualified as pathological by a specialist in the field, such as a dermatologist. It is therefore a use on healthy skin and/or mucosa.

By "healthy skin and/or mucosa" is meant herein all or part of a healthy area of skin and/or mucosa, therefore with no infections, scars, skin diseases or conditions such as candidiasis, impetigo, psoriasis, eczema, acne, ichthyosis, gingivitis or dermatitis or wounds or injuries or canker sores or ulceration or burning and/or other dermatoses, or aphthoses or inflammation or irritation.

In a particular embodiment, said cosmetic care method is for the care of the unaesthetic and/or unpleasant and/or uncomfortable manifestations of sensitive, sensitized, fragile and/or weakened skin and/or mucosa, as defined above.

Unaesthetic and/or unpleasant and/or uncomfortable manifestations of sensitive, sensitized, fragile and/or weakened skin and/or mucosa are well-known from the skilled person and typically include the feeling of heat or warmth or tension, tingling, stinging, tightness, itching, pruritus, dry patches, erythema, redness and a mixture of these manifestations. As will be noted by the skilled person, such manifestations may resemble some symptoms of some particular skin and/or mucosa disease. However, in the context of the present invention, said unaesthetic and/or unpleasant and/or uncomfortable manifestations are only cared at a cosmetic scale, in the context of a sensitive, sensitized, fragile and/or weakened skin and/or mucosa and not in the context of a pathological skin and/or mucosa.

Therefore, in a particular embodiment, the unaesthetic and/or unpleasant and/or uncomfortable manifestations of sensitive, sensitized, fragile and/or weakened skin and/or mucosa to be cared by the cosmetic care method of the invention are chosen from the feeling of heat or warmth or tension, tingling, stinging, tightness, itching, pruritus, dry patches, erythema, redness and a mixture of these manifestations.

In an alternative embodiment, the cosmetic care method of the invention is for controlling and/or reducing body odor.

By "body odor" is meant herein the odors emanating from the body, such as, as non limiting examples, the ones resulting of sweat, sebaceous and senile glands emission combined with metabolic activity of the microbiota.

In a particular embodiment, the body odor emanates from the foot or the armpit.

Exemplary genuses of odor generating bacteria include, but are not limited to *Staphylococcus, Propionibacterium, Bacillus* and *Corynebacterium*. Specific examples of under-arm odor generating bacteria include, but are not limited to *C. jeikeium, C. striatum, C. bovis, C. xerosis, C. tuberculostearicum, C. minutissimum, S. epidermidis, S. haemolyticus* and *Bacillus licheniformis*. Specific examples of foot odor generating bacteria include those that produce isovaleric acid and/or propionic acid, including but not limited to *Bacillus subtilis, P. avidum, S. epidermidis, S. hominis* and *Corynebacterium* sp. H996.

In a particular embodiment, said postbiotic composition of the invention is highly specific towards odor-generating bacteria and does not affect negatively non-odor-generating bacteria.

In an alternative embodiment, the cosmetic care method of the invention is for preventing, reducing and/or eliminating dandruffs.

By "dandruffs" is meant herein a state of the skin mainly affecting the scalp which manifestations include flaking and mid itchiness. Microorganisms involved in dandruffs production include *Malassezia globosa*.

In a particular embodiment, the cosmetic care method of the invention is for the care of an unaesthetic and/or unpleasant and/or uncomfortable manifestation of a subject's skin and/or mucosa, due to dysbiosis in said subject, in particular due to skin and/or mucosa dysbiosis.

By "dysbiosis" is meant herein, a microbial imbalance or maladaptation on or inside the body.

In a particular embodiment, the cosmetic care method of the invention is for the care of an unaesthetic and/or unpleasant and/or uncomfortable manifestation of oily skin.

In a particular embodiment, the cosmetic care method of the invention is for the care of progressive macular hypomelanosis (PMH).

The subject according to the invention is an animal, preferably a mammal, even more preferably a human. However, the term "subject" can also refer to non-human animals, in particular mammals such as dogs, cats, horses, cows, pigs, sheeps, donkeys, rabbits, ferrets, gerbils, hamsters, chinchillas, rats, mice, guinea pigs and non-human primates, among others, or non mammals such as poultry.

In a particular embodiment of the cosmetic care method of the invention, said postbiotic composition is applied on the skin and/or mucosa.

Alternatively, said postbiotic composition may be administered orally, intranasally, sublingually, or transdermally (for example using a transdermal patch).

In a particularly preferred embodiment, said postbiotic composition is in the form of a cosmetic composition for topical application.

Cosmetic Care Formulation

The present invention also concerns a formulation, in particular a cosmetic care formulation, for topical application comprising:
 (i) a postbiotic composition, comprising at least one postbiotic, in particular engineered postbiotic, as defined in the section "Engineered postbiotic" above, and at least one bacteriocin and/or endolysin, as defined in the section "Engineered postbiotic" above,
 (ii) at least one cosmetically acceptable excipient and/or adjuvant selected from the group consisting of fatty substances, thickeners, emulsifiers, colorants, preservatives, perfumes and combinations thereof, and
 (iii) optionally an additional active ingredient for the cosmetic care of the skin and/or mucosa.

In a particular embodiment, said postbiotic, in particular engineered postbiotic, is obtained from microorganisms, in particular bacteria, heterologously expressing said at least one bacteriocin and/or endolysin, as defined in the section "Engineered postbiotic" above. In a particular embodiment, said postbiotic, in particular engineered postbiotic, comprises at least one microbial, in particular bacterial, lysate, as defined in the section "Engineered postbiotic" above, preferably obtained from microorganisms, in particular bacteria, heterologously expressing said at least one bacteriocin and/or endolysin, as defined in the section "Engineered postbiotic" above.

In a particular embodiment, said postbiotic is obtained from *L. rhamnosus* bacteria, in particular *L. rhamnosus* GG bacteria, heterologously expressing said at least one bacteriocin and/or endolysin, as defined in the section "Engineered postbiotic" above, more particularly expressing lysostaphin. In a particular embodiment, said postbiotic, in particular engineered postbiotic, comprises at least one bacterial lysate obtained from *L. rhamnosus* bacteria, in particular *L. rhamnosus* GG bacteria, heterologously expressing said at least one bacteriocin and/or endolysin, as defined in the section "Engineered postbiotic" above, more particularly expressing lysostaphin.

By "cosmetic formulation" is meant herein a composition intended to procure a cosmetic effect, in particular in the context of a topical application.

By "cosmetically acceptable excipient" is meant herein a substance that is non-toxic, biologically tolerable, and otherwise biologically suitable for administration to a subject, such as an inert substance, added to a cosmetic composition or otherwise used as a vehicle, carrier, or diluents to facilitate administration of a cosmetically active ingredient and that is compatible therewith.

By "cosmetically acceptable adjuvant" is meant herein a substance that is non-toxic, biologically tolerable, and otherwise biologically suitable for administration to a subject, added to a cosmetic composition to strengthen the role of the excipient or of a cosmetically active ingredient.

Examples of fatty substances usable in the context of the invention include oils or mineral waxes, animal or vegetable fatty acids, fatty acid esters such as triglycerides of fatty acids having from 6 to 18 carbon atoms or fatty alcohols. Examples of fats and mineral oils that can be used include vaseline oil. Examples of animal oils that can be used include whale oil, seal, menhaden, halibut liver, cod, tuna, turtle, ox foot, horse foot, sheep foot, mink, otter, marmot, etc. Examples of vegetable oils that can be used include almond oil, wheat germ, olive, com germ, jojoba, sesame, sunflower, palm nuts, shea shorea, macadamia, blackcurrant seed and the like. Examples of fatty acid esters that can be used include acid esters $C_{12}$-$C_{22}$ saturated or unsaturated lower alcohols such as isopropanol or glycerol or fatty alcohols of $C_8$-$C_{22}$, linear or branched, saturated or unsaturated alkanediols or 1,2-$C_{10}$-$C_{22}$. Additional examples of fats are petrolatum, paraffin, lanolin, hydrogenated lanolin, tallow, acetylated lanolin and silicone oils. Examples of waxes that can be used include Sipol wax, lanolin wax, beeswax, candelilla wax, microcrystalline wax, carnauba wax, spermaceti, cocoa butter, shea butter, silicone waxes, hydrogenated oils solid at 25° C., sugar glycerides, oleates, myristates, linoleates and stearates of Ca, Mg and Al. Examples of fatty alcohols that can be used include lauryl, cetyl, myristyl, stearyl, palmityl and oleyl alcohols such as 2-octyldodecanol, 2-decyl tetradecanol or 2-hexyl decanol.

Thickeners include substances which can increase the viscosity of a composition, without substantially modifying the efficacy of the ingredients within the composition. Thickeners can also increase the stability of the compositions of the present invention. Examples of thickeners usable in the context of the invention include crosslinked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Examples of natural gums suitable for use in the present invention include guar, xanthan, sclerotium, carrageenan, pectin and combinations thereof.

An emulsifier is particularly suitable when the composition is in the form of an emulsion or if immiscible materials are being combined. Emulsifiers can be nonionic, anionic or cationic. Examples of emulsifiers include esters of polyglycols and of fatty acids, including saturated or unsaturated $C_{12-30}$ fatty acids (e.g., oleic acid, cetylic acid, stearic acid) and polyglycols comprising n number of oxyalkylene groups wherein n is an integer from 1 to 200 or alternately, 1 to 50 (e.g., 1 to 20 oxyethylene groups); compounds with the INCI name PEG-n stearate or PEG-n oleate; polyethylene glycol-8 monostearate, polyethylene glycol-10, or polyethylene glycol-12 distearate; ethers of polyglycols and of fatty alcohols which are glycosylated, including $C_{12-30}$ alcohols having from 1 to 10 glycosyl groups and polyglycols comprising n number of oxyalkylene groups wherein n is an integer from 1 to 200 (e.g., 1 to 20 oxy ethylene groups) such as polyoxyethylenated (20 OE) methyl glucose distearate; esters of polyglycols and of fatty acids which are glycosylated, including $C_{12-30}$ fatty acids having from 1 to 10 glycosyl groups and polyglycols comprising n number of oxyalkylene groups wherein n is an integer from 1 to 200 (e.g., 1 to 20 oxy ethylene groups); ethers of $C_{12-30}$ alcohols and of glycerol or of polyglycerol such as polyglyceryl-3 cetyl ether; esters of $C_{12-30}$ fatty acids and of glycerol or of polyglycerol, including esters comprising from 1 to 10 glycerol groups such as hexa-glyceryl monosterate, diglyceryl distearate, tetraglyceryl tristearate, decaglyceryl decasteartate, diglyceryl monostearate, hexaglyceryl tristearate, decaglyceryl pentastearate, the ester of glycerol and of palmitic and stearic acids, and glyceryl mono-and dibehenate; ethers of oxyalkylene-modified $C_{12-30}$ alcohols and of glycerol or polyglycerol; ethers of $C_{12-30}$ fatty alcohols and of sucrose or glucose, such as compounds with the INCI names of $C_{12-30}$ alkylglucoside, $C_{12-30}$ alkylglucoside, cetearyl glucoside, myristyl glucoside or cetearyl glucoside; esters of sucrose and of $C_{12-30}$ fatty acids, such as sucrose distearate or sucrose tristearate, sucrose cocoate, sucrose dilaurate, sucrose distearate, sucrose hexaerucate, sucrose hexapalmitate, sucrose laurate, sucrose mortierellate, sucrose myristate, sucrose oleate, sucrose palmitate, sucrose pentaerucate, sucrose polybehenate, sucrose polycottonseedate, sucrose polylaurate, sucrose polylinoleate, sucrose polyoleate, sucrose polypalmate, sucrose polysoyate, sucrose polystearate, sucrose ricinoleate, sucrose stearate, sucrose tetraisostearate, and sucrose trilaurate; esters of pentaerythritol and of $C_{12-30}$ fatty acids, such as pentaerythritol tetrastearate; esters of sorbitol and/or of sorbitan and of $C_{12-30}$ fatty acids, such as sorbitan monostearate, sorbitan tristearate, or sorbitan laurate; ethers of sorbitol and/or of sorbitan and of alkoxylated sorbitan; esters of $C_{12-30}$ fatty acids and of alkoxylated ethers of sorbitol such as polysorbate-60, polysorbate-61, sorbeth-3 isostearate, polyoxyethylenated 4 OE sorbitan monostearate, polyoxyethylenated 20 OE sorbitan tristearate, cetearths, ceteths, laneths, laureths such as laureth-7, isostearths and stearths.

Non-limiting examples of colorants that can be used in the context of the present invention include those known to a person of ordinary skill in the art (see, e.g., CTFA International Cosmetic Ingredient Dictionary and Handbook (2004)). For instance natural and synthetic pigments and lakes can be used. Examples of groups of pigments include carbon, cadmium, iron oxide, Prussian blue, chromium, cobalt, copper, titanium, ultramarine, zinc, clay earth, and organic pigments. Specific non-limiting examples of colorants include Aluminum Powder, Blue 1 Lake, Bronze Powder, Chromium Oxide Greens, Copper Powder, Ext. Yellow 7 Lake, Green 3 Lake, Orange 4 Lake, Orange 5 Lake, Orange 10 Lake, Pigment Blue 15, Pigment Blue 15:2, Pigment green 7, Pigment Orange 5, Pigment Red 4, Pigment Red 5, Pigment Red 48, Pigment Red 53, Pigment Red 53:1, Pigment Red 57, Pigment Red 57:1, Pigment Red 63:1, Pigment Red 64:1, Pigment Red 68, Pigment Red 83, Pigment Red 88, Pigment Red 90:1 Aluminum Lake, Pigment Red 112, Pigment Red 172 Aluminum Lake, Pigment Red 173 Aluminum Lake, Pigment Red 190, Pigment Violet 19, Pigment Yellow 1, Pigment Yellow 3, Pigment Yellow 12, Pigment Yellow 13, Pigment Yellow 73, Red 4 Lake, Red 6 Lake, Red 7 Lake, Red 21 Lake, Red 22 Lake, Red 27 Lake, Red 28 Lake, Red 30 Lake, Red 31 Lake, Red 33 Lake, Red 34 Lake, Red 36 Lake, Red 40 Lake, Sunset Yellow Aluminum Lake, Yellow 5 Lake, Yellow 6 Lake, Yellow 7 Lake, Yellow 10 Lake, and Zinc Oxide.

Non-limiting examples of preservatives that can be used in the context of the present invention include quaternary ammonium preservatives (e.g., polyquaternium-1), parabens (e.g., methylparabens and propylparabens), phenoxyethanol, benzyl alcohol, chlorobutanol, phenol, sorbic acid, thimerosal, potassium sorbate, or combinations thereof.

In the context of the invention, the term "perfume" refers to any substance that is liable to release a pleasant odor. Perfumes of natural or synthetic origin and mixtures thereof may be used. Examples of perfumes of natural origin that may be mentioned include extracts from flowers, from stems and leaves, from fruit, from fruit peel, from roots, from wood, from grasses and gramineae, from needles and branches, and from resins and balms. Examples of perfumes of synthetic origin that may be mentioned include compounds of the ester, ether, aldehyde, ketone, aromatic alcohol and hydrocarbon type, and mixtures thereof. Esters that may be mentioned in particular include benzyl acetate, benzyl benzoate, phenoxyethyl isobutyrate, p-tert-butylcyclohexyl acetate, citronellyl acetate, citronellyl formate, geranyl acetate, linalyl acetate, dimethylbenzylcarbinyl acetate, phenylethyl acetate, linalyl benzoate, benzyl formate, ethylmethylphenyl glycinate, alkylcyclohexyl propionate, styrallyl propionate and benzyl salicylate. An ether that may be mentioned is benzyl ethyl ether. Examples of aldehydes that may be mentioned include linear alkanals comprising from 8 to 18 carbon atoms, citral, citronellal, citronellyloxyacetaldehyde, cyclamenaldehyde, hydroxycitronellal, lilial and bourgeonal. Examples of ketones that may be mentioned include ionones, for instance alpha-isomethylionone and methyl cedryl ketone. Among the aromatic and especially terpenic alcohols, mention may be made of anethole, citronellol, eugenol, isoeugenol, geraniol, linalool, phenylethyl alcohol and terpineol. Hydrocarbons that may especially be mentioned are terpenes. Moreover, it is also possible to use essential oils, aroma components, for instance essences of sage, camomile, clove, balm, mint, cinnamon leaves, lime tree blossom, juniper, vetiver, olibanum, galbanum, labolanum and lavandin. Essence of bergamot, dihydromyrcenol,lilial, lyral, citronellol, phenylethyl alcohol, alpha-hexylcinnamaldehyde, geraniol, benzylacetone, cyclamenaldehyde, linalool, ambroxane, indol, hedione, sandelice, essences of lemon, mandarin and orange, allylamine glycolate, cyclovertal, essence of lavandin, essence of sage, beta-damascone, essence of geranium, cyclohexyl salicylate, phenylacetic acid, geranyl acetate, benzyl acetate and rose oxide can be used for example as perfume, alone or as a mixture.

In a particular embodiment, said formulation may further comprise additional cosmetically acceptable excipients selected from binders, bulking agents, emollients/humectants/moisturizers, absorbents, chelating agents, denaturants, solubilizing agents, buffering agents and solvents.

By "binder" is meant herein an excipient holding the ingredients of a formulation together. Examples of binders include povidone, pregelatinized starch, dextrin, gelatin, hydroxypropyl methylcellulose, maltodextrin, starch, zein, acacia, alginic acid, carbomers (cross-linked polyacrylates), polyacrylamide, polymethacrylates, carboxymethylcellulose sodium, ethylcellulose, guar gum, cellulose gum, xanthan gum, hydrogenated vegetable oil (type 1), hydroxyethyl cellulose, hydroxypropyl cellulose, methylcellulose, magnesium aluminum silicate, and/or sodium alginate.

By "bulking agent" or "filler" is meant herein an excipient used to increase the volume of the material to enable easier processing of the ingredients and make it into a size suitable for consumption. Non-limiting examples of fillers include carbohydrates, inorganic compounds, and polyvinylpirrolydone. Other non-limiting examples of fillers include dibasic calcium sulfate, tribasic calcium sulfate, starch, calcium carbonate, magnesium carbonate, microcrystalline cellulose, dibasic calcium phosphate, tribasic calcium phosphate, magnesium carbonate, magnesium oxide, calcium silicate, talc, modified starches, lactose, sucrose, mannitol, and sorbitol.

Examples of emollients/humectants/moisturizers include phospholipids, ceramide, glycerin, cetyl alcohol, cetearyl isononanoate, cetearyl octanoate, decyl oleate, isooctyl stearate, coco caprylate/caprate, ethylhexyl hydroxystearate, ethylhexyl isononanoate, isproyl palmitate, isopropyl isostearate, isopropyl myristate, oleyl oleate, hexyl laurate, paraffinum liquidum, C13-14 isoparaffin, PEG-75 lanolin, PEG-7 glyceryl cocoate, petrolatum, ozokerite, cyclomethicone, dimethicone, dimethicone copolyol, dicaprylyl ether, *Butyrospermum parkii, Buxus chinensis, canola*, carnauba *cera, Copernicia cerifera, Oenothera biennis, Elaeis guineensis, Prunus dulcis*, squalane, *Zea mays, Glycine soja, Helianthus annuus* seed oil, lanolin, hydrogenated *castor* oil, hydrogenated coconut oil, avocado oil, hydrogenated polyisobutene, sucrose cocoate, stearoxy dimethicone, lanolin alcohol, isohexadecane, butylene glycol, caprylic/capric triglyceride, dimyristyl tartrate, glucose, glycereth-26, glyceryl stearate, hydrolyzed milk protein, lactic acid, lactose and other sugars, laureth-8, lecithin, octoxyglycerin, PEG-12, PEG-135, PEG-150, PEG-20, PEG-8, caprylyl glycol, pentylene glycol, hexylene glycol, phytantriol, polyquaternium-39, PPG-20 methyl glucose ether, propylene glycol, sodium hyaluronate, sodium lactate, sodium PCA (sodium salt of 1-pyrrolidone carboxylic acid), sorbitol, succinoglycan, synthetic beeswax, tri-C14 15 alkyl citrate and starch.

Examples of absorbents include alumina, aluminum hydroxide, aluminum magnesium silicate, aluminum silicate, aluminum starch octenylsuccinate, bentonite, bismuth oxychloride, boron nitride, calcium carbonate, clay, cornstarch, fuller's earth, kaolin, magnesium, magnesium carbonate, magnesium hydroxide, montmorillonite, rice starch, silica, silicate, silt, sodium carbonate, talc and zeolite.

Examples of chelating agents include ethylene diaminetetraacetic acid (EDTA), sodium or potassium salts of EDTA such as EDTA disodium salt, EDTA trisodium salt and EDTA tetrasodium salt, cyclodextrin, pentasodium pentetate, phytic acid, potassium citrate, sodium gluconate and potassium gluconate.

Examples of solubilizing agents include polyethylene glycol, polyvinylpyrrolidone, dextran, or mixtures thereof.

Examples of buffering agents include sodium bicarbonate, potassium bicarbonate, magnesium hydroxide, magnesium lactate, magnesium gluconate, aluminum hydroxide, aluminum hydroxide/sodium bicarbonate co precipitate, a mixture of an amino acid and a buffer, a mixture of aluminum glycinate and a buffer, a mixture of an acid salt of an amino acid and a buffer, a mixture of an alkali salt of an amino acid and a buffer, sodium citrate, sodium tartarate, acetic acid and acetates of sodium, sodium carbonate, sodium polyphosphate, potassium polyphosphate, sodium pyrophosphate, potassium pyrophosphate, disodium hydrogen phosphate, dipotassium hydrogenphosphate, trisodium phosphate, tripotassium phosphate, potassium metaphosphate, magnesium oxide, magnesium hydroxide, magnesium carbonate, magnesium silicate, calcium acetate, calcium glycerophosphate, calcium chloride, calcium hydroxide, calcium lactate, calcium carbonate, calcium bicarbonate, and other calcium salts, citric acid and citrates of sodium or potassium, phosphoric acid and phosphates of sodium and of potassium.

Examples of solvents include water and aqueous solvents such as n-butanol, isopropyl alcohol, n-propanol, ethanol, 1,2-hexanediol and methanol.

By "additional active ingredient for the cosmetic care of the skin and/or mucosa" is meant herein an ingredient having a beneficial effect on the cosmetic care of the skin and/or mucosa, said ingredient being different from the postbiotic composition, as defined in the section "Engineered postbiotic" above, in particular from the postbiotic as defined in the section "Engineered postbiotic" above and from the at least one bacteriocin and/or endolysin as defined in the section "Engineered postbiotic" above. In a particular embodiment, said additional active ingredient targets the same unaesthetic manifestations as the postbiotic composition of the invention. In an alternative embodiment, said additional active ingredient targets different unaesthetic manifestations than the postbiotic composition of the invention.

Examples of such additional active ingredients for the cosmetic care of the skin and/or mucosa include anti-aging ingredients, in particular ingredients for preventing, correcting or slowing down the effects of skin ageing, e.g. vitamin A, vitamin E or vitamin C; ingredients which effects skin revitalization care, such as madecassoside; moisturizers such as ecdysteroid or a plant extract containing it (for example an extract of Ajuga turkestanica), propylene glycol, butylene glycol, pentylene glycol and their mixtures in all proportions, in particular those available commercially of PEG-60 type; an ingredient having a depigmenting activity or a lightning activity on the skin such as ascorbic acid derivatives, in particular esters (for example ascorbyl glucosides and ascorbyl phosphates, in particular magnesium ascorbyl phosphate) and an extract of fruit or of flowers of black elder (Sambucus nigra); an ingredient having a slimming activity such as xanthine, in particular caffeine; an ingredient having a calming, soothing or relaxing activity such as glycyrrhizate, in particular in the form of a potassium salt; an ingredient having an activity in stimulating skin microcirculation in order to improve the radiance of the complexion, in particular of the face, such as ruscogenin; an ingredient having a seboregulating activity such as zinc oxide or at least one zinc-based derivative, in particular organic zinc salts, such as zinc gluconate, zinc salicylate or zinc pidolate; an ingredient intended to clean or purify the skin; a refreshing agent such as menthol or a derivative of the latter, such as menthoxypropanediol; an anti-wrinkle ingredient; an exfoliator, or a skin conditioning agent such as urea, guanidine, aloe vera, glycolic acid and glycolate salts such as ammonium and quaternary alkyl ammonium, lactic acid and lactate salts such as sodium lactate, ammonium lactate and quaternary alkyl ammonium lactate, polyhydroxy alcohols such as sorbitol, glycerol, hexanetriol, tocopherol, propylene glycol, butylene glycol, hexylene glycol, polyethylene glycol, carbohydrates such as alkoxylated glucose, starches, starch derivatives, glycerin, pyrrolidone carboxylic acid (PCA), lactamide monoethanolamine, acetamide monoethanolamine, volatile silicone oils, non-volatile silicone oils, *Helianthus annuus* seed oil, phospholipids, *Salix alba* (willow) bark extract, glycine soja seed extract, and mixtures thereof.

Additional cosmetically active ingredients usable in the context of the invention further include probiotics, as defined in the section "Engineered postbiotics" above, in particular live probiotics; and prebiotics (different from the postbiotic as defined in the section "Engineered postbiotic" above).

Examples of suitable additional prebiotics typically include amino acids, biotin, fructo-oligosaccharide, galacto-oligosaccharides, hemicelluloses (e.g., arabinoxylan, xylan, xyloglucan, and glucomannan), inulin, chitin, lactulose, mannan oligosaccharides, oligofructose-enriched inulin, gums (e.g., guar gum, gum arabic and carregenaan), oligofructose, oligodextrose, tagatose, resistant maltodextrins (e.g., resistant starch), trans- galactooligosaccharide, pectins (e.g., xylogalactouronan, citrus pectin, apple pectin, and rhamnogalacturonan-I), dietary fibers (e.g., soy fiber, sugarbeet fiber, pea fiber, corn bran, and oat fiber) and xylooligosaccharides.

In a particular embodiment, the formulation of the invention comprises at least 0.2% of postbiotic composition of the invention, in particular at least 0.5%, at least 1%, at least 3%, at least 5%, at least 10%, at least 15%, at least 20%, at least 30%, at least 40% or at least 50% of postbiotic composition of the invention.

In a particular embodiment, the formulation of the invention comprises between 0.2% and 20% of postbiotic composition of the invention, more particularly between 0.3% and 15% of postbiotic composition of the invention, still particularly between 0.5% and 10% of postbiotic composition of the invention, still particularly between 1% and 8% of postbiotic composition of the invention, still particularly between 3% and 5% of postbiotic composition of the invention.

The cosmetic formulation of the invention can be formulated under any suitable form well-known from the skilled person.

In a particular embodiment, said formulation is in the form of aqueous, hydroalcoholic or oily solutions, of dispersions in the form of solutions or dispersions of the lotion or serum type, of emulsions in particular with liquid or semi-liquid consistency of the milk type, typically obtained by dispersion of a fatty phase in an aqueous phase (O/W) or conversely (W/O), or suspensions or emulsions of soft semi-solid or solid consistency of the cream type, of cream, of aqueous or anhydrous gel, of microemulsions, of nanoemulsions, of microcapsules, of microparticles, of ionic and/or nonionic type vesicular dispersions, of stick, of aerosol spray, of pump spray, or of foam. In a particular embodiment, said formulation is in the form of an emulsion, of a microemulsion or of a nanoemulsion.

The cosmetic formulation of the invention can typically be in the form of a toner, gel, jelly masque, clay masque, lotion, cream, lipstick, foundation, pressed powder, loose powder, makeup cosmetics, makeup-removing oil, makeup removing lotion, facial cleanser, bodywash, shampoo, suntan lotion or hand cream, but it is not limited thereto.

The cosmetic formulation according to the present invention can be prepared by mixing the essential ingredient(s), and optional ingredient(s), if necessary.

The method and means to mix the above essential and optional ingredients are not limited. Any conventional method and means can be used to mix the above essential and optional ingredients to prepare the formulation according to the present invention.

In a particular embodiment, the formulation of the invention is in a form imbuing a solid substrate, in particular a substrate formed from synthetic materials or formed from natural biodegradable and sustainably sourced natural originated fiber, natural fiber, or regenerated or recycled natural fiber, such as a wipe.

As used herein, the terms "comprising," "having," and "including" are used in their open, non-limiting sense. The terms "a," "an," and "the" are understood to encompass the plural as well as the singular. The expression "at least one" means one or more and thus includes individual components as well as mixtures/combinations.

All ranges and values disclosed herein are inclusive and combinable. For example, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The present disclosure will be further illustrated by the examples below.

BRIEF DESCRIPTION OF THE FIGURES

FIG. 4: Measurement of *S. aureus* turbidity reduction with time for *L. rhamnosus* GG lysate (concentrated 40×) and 20 mM acetate buffer pH 5 with or without lysostaphin (1 µg/mL). Time to reduce by half initial absorbance (IC50) is lower for Lysostaphin in lysate compared to Lysostaphin in acetate buffer. Lysate and acetate buffer in absence of Lysostaphin have identical 1050. FIG. 5: Measurement of *S. aureus* CFU reduction with time for *L. rhamnosus* GG lysate (concentrated 40×) and 20 mM acetate buffer pH 5 with or without Lysostaphin (1 µg/mL)

EXAMPLES

Figure 1:
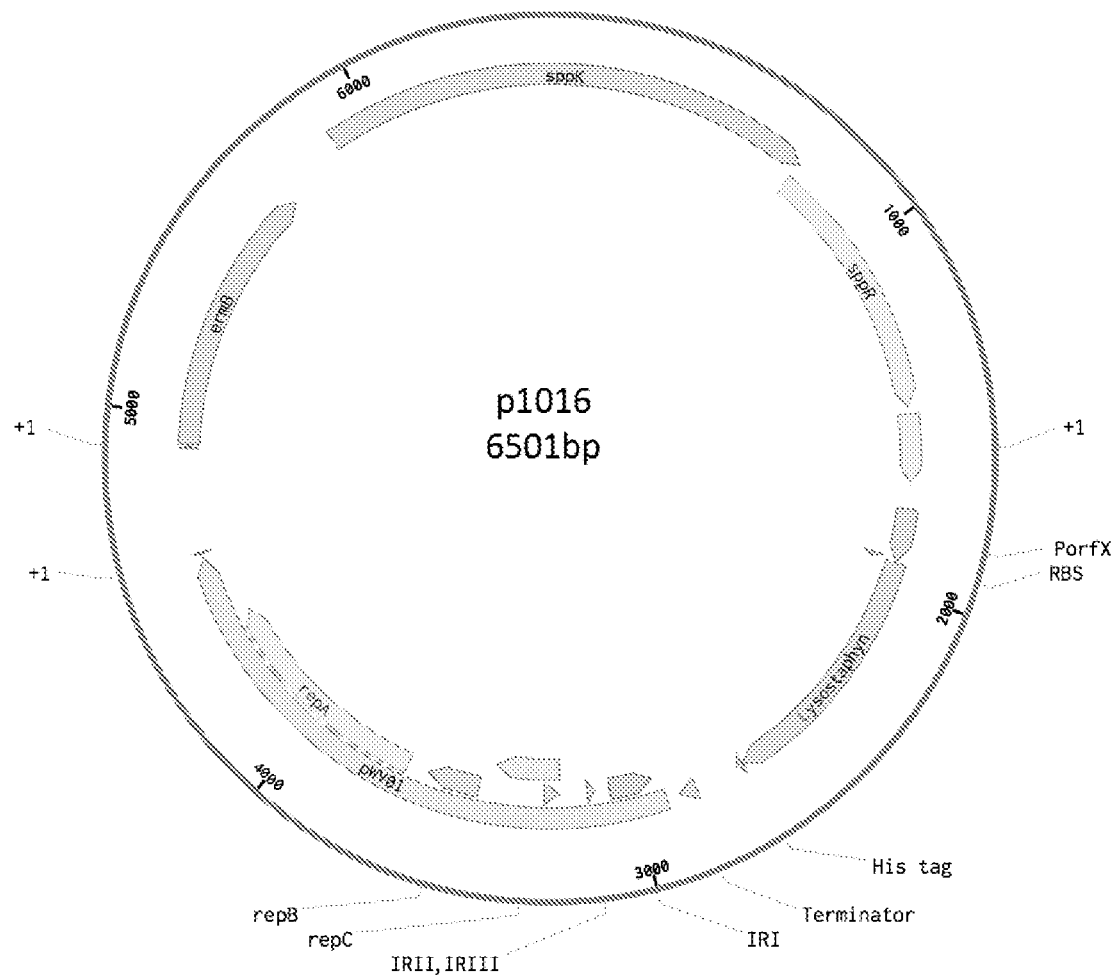
FIG. 1: Lysostaphin expression plasmid. p1016 plasmid map with His tagged lysostaphin expressed from PorfX IP-673 inducible promoter. Plasmid backbone contains pWV01 origin of replication and an erythromycin resistance marker (ermB).

In the present examples, the inventors developed engineered postbiotics suitable to tackle causes, symptoms and recurrence of unaesthetic manifestations of skin dysbiosis due to the growth of *S. aureus*, and demonstrated:
  a *S. aureus* specific killing activity based on a lysate containing Lysostaphin,
  a synergistic increase in Lysostaphin killing activity in presence of bacterial lysate,
  a beneficial effect on host commensal microbiota, and
  a soothing effect on irritated skin after skin tape-stripping As a proof of principle, probiotic strain *L. rhamnosus* GG (LrOs11721) was engineered to express, in the cytoplasm, lysostaphin, a bacteriocin with high specificity for *S. aureus*. Lysostaphin was cloned on a plasmid (FIG. 1) under the control of the sakacin inducible promoter PorfX (Sørvig et al. (2005) Microbiology (Reading, England) 151:2439-2449) and transformed into *L. rhamnosus*. Transformants were grown, lysostaphin expression was induced at mid-log phase and cells were harvested at high density (OD~1). Bacterial cells were concentrated 40× in 20 mM acetate buffer pH 5 by centrifugation before being lysed mechanically and filtered sterilized leading to a lysate (herein called lysolysate) containing both *L. rhamnosus* cell components and Lysostaphin.

EXAMPLE 1

*S. aureus* Specific Killing Using a *L. rhamnosus* Lysolysate

Figure 2:
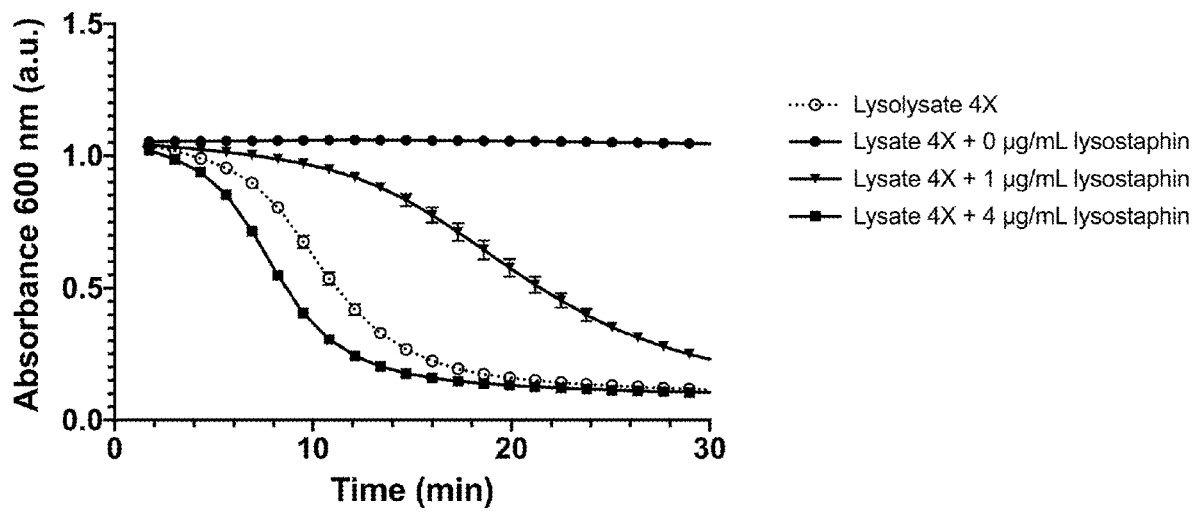
FIG. 2: Lysolysate killing activity on *S. aureus*. Measurement of *S. aureus* turbidity reduction with time when mixing *S. aureus* Newman strain with *L. rhamnosus* lysolysate produced from lysed culture of *L. rhamnosus* GG LrOs11721+ p1016 expressing lysostaphin and concentrated 40× in 20 mM acetate buffer pH 5. *L. rhamnosus* GG LrOs11721 lysate was used as control and *L. rhamnosus* GG LrOs11721 lysates spiked with lysostaphin (1 and 4 µg/mL final concentration) as references.

In order to check the staphylolytic activity of the lysolysate, a turbidity reduction experiment was performed using *S. aureus* Newman strain mixed with lysolysate (FIG. 2). As shown in FIG. 2, a rapid decrease of the *S. aureus* population, as measured by absorbance at 600 nm, can be observed in presence of the lysolysate. No decrease in absorbance was observed when *S. aureus* cells were put in presence of the *L. rhamnosus* lysate indicating that the expressed Lysostaphin is responsible for the turbidity reduction and so the staphylolytic activity. Inventors decided to test the lysolysate killing specificity towards *S. aureus*.

Figure 3:
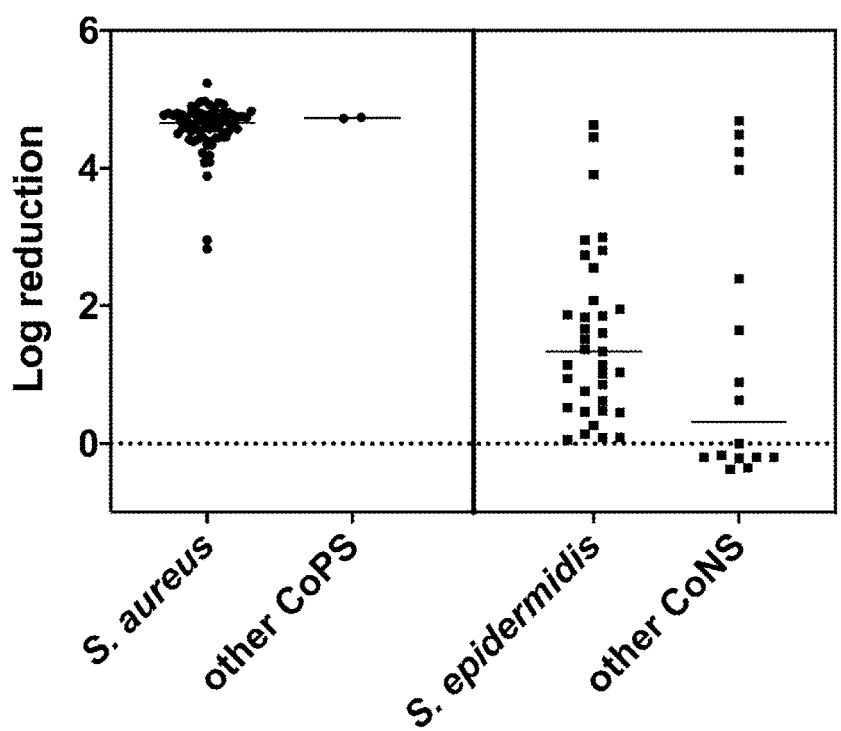
FIG. 3: Lysolysate specific and efficient killing of *S. aureus*. Log reduction (−log10 (Final CFU/Initial CFU)) in *S. aureus* and other staphylococcal strains after 1 hour incubation with lysolysate.

Specificity of endolysin is generally at the genus level meaning that for example staphylococcal endolysins are able to kill both non-commensal species such as *S. aureus* but also commensal species such as *S. epidermidis*. Unlike endolysins, lysostaphin has been shown to be specifically targeting *S. aureus* and show a much lower activity against other *Staphylococcal* species such as *S. epidermidis*. To test if the Lysostaphin-containing *L. rhamnosus* lysate has also a high *S. aureus* specificity, a killing assay was performed (FIG. 3) using lysolysate in presence of both Coagulase positive strains (CoPS) among which 75 *S. aureus* strains and Coagulase negative strains (CoNS) among which 35 *S. epidermidis* strains. An average of 4.58 log reduction was obtained for *S. aureus* strains against a 1.54 log reduction obtained against the 35 *S. epidermidis* strains. Thus lysolysate shows a high specificity towards *S. aureus* species.

Figure 4:
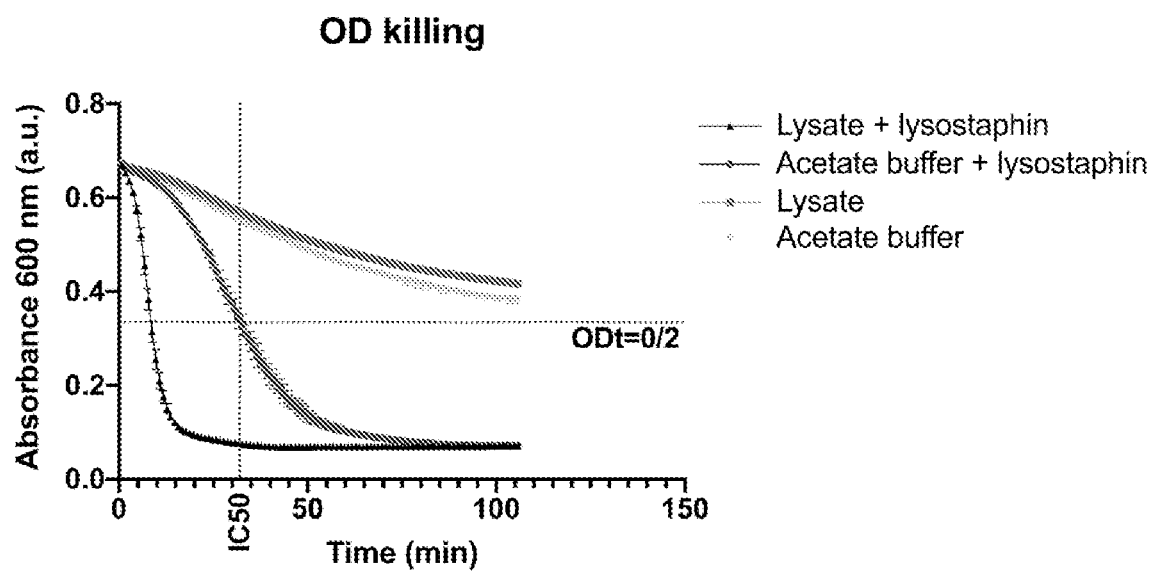
FIGS. 4-5: Synergistic effect of lysostaphin and bacterial lysates.
Figure 5:
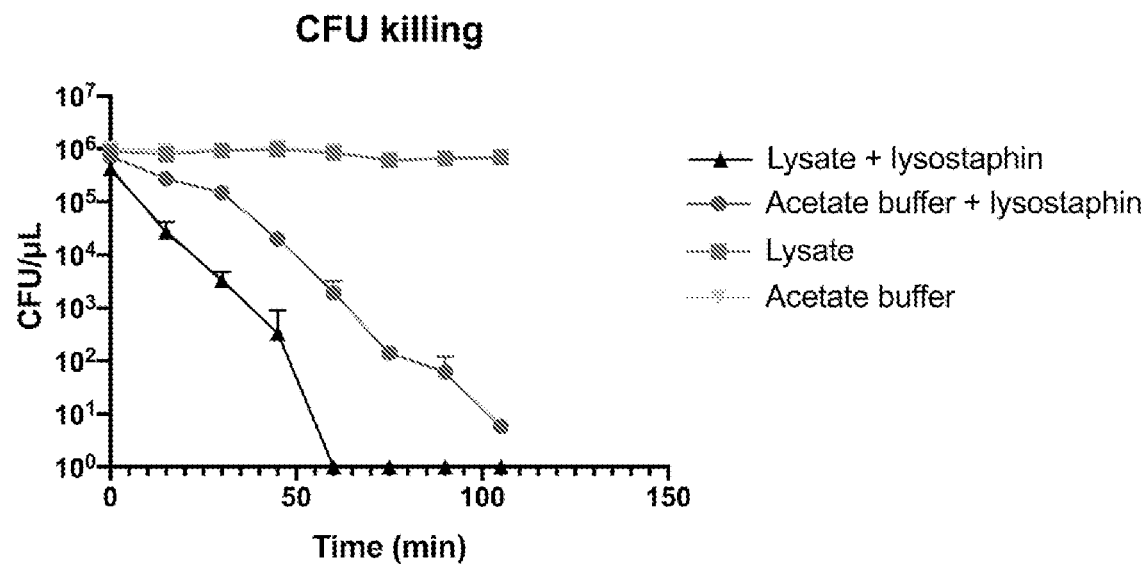

To quantify the effect of the bacterial lysate on lysostaphin activity, a turbidity reduction experiment and a CFU experiment were performed (FIG. 4-5). The IC50, time to decrease initial OD by half, was measured for the *L. rhamnosus* lysate alone, 20 µg/ml of purified Lysostaphin (Sigma reference L9043) resuspended in 20 mM acetate buffer pH 5 (NaOAc) buffer and 20 µg/ml of purified Lysostaphin resuspended in *L. rhamnosus* lysate. Surprisingly, the inventors observed a higher turbidity reduction (lower IC50) and a faster decrease in CFU for the Lysostaphin in lysate compared to Lysostaphin in acetate buffer. No difference in absorbance or CFU counts were measured between *L. rhamnosus* lysate and acetate buffer indicating that there is no activity of the *L. rhamnosus* lysate alone and the improvement of Lysostaphin activity in lysate is not the result of an additive effect of Lysostaphin activity and *L. rhamnosus* lysate activity but rather a synergistic effect of the lysate on the Lysostaphin activity. Such synergistic effect of Lysostaphin and bacterial lysate has not been documented and offer an advantageous and non-obvious effect for the killing of S. aureus with lysolysate compare to Lysostaphin alone.

Figure 6:
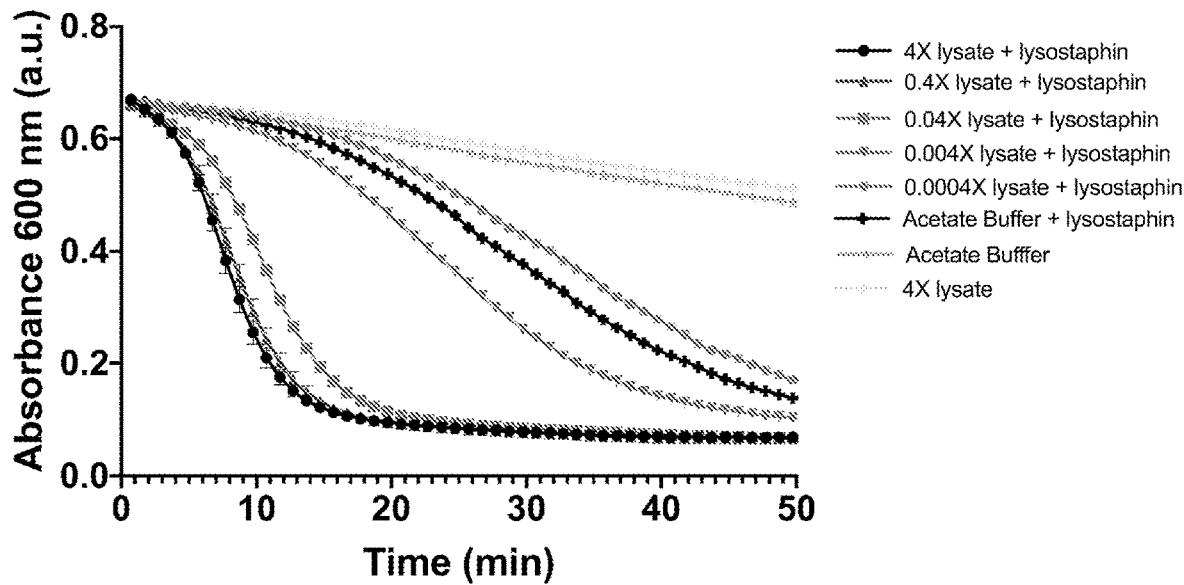
FIG. 6: Effect of lysate concentration on synergy. Measurement of *S. aureus* turbidity reduction with time for different concentrations of *L. rhamnosus* GG lysate (4×, 0.4×, 0.04×, 0.004× 0.0004×) supplemented with Lysostaphin (1 µg/mL final concentration). Below a given concentration of lysate (between 0.004× and 0.0004×) the Lysostaphin killing activity is equivalent or lower than the same Lysostaphin concentration in acetate buffer.
Figure 7:
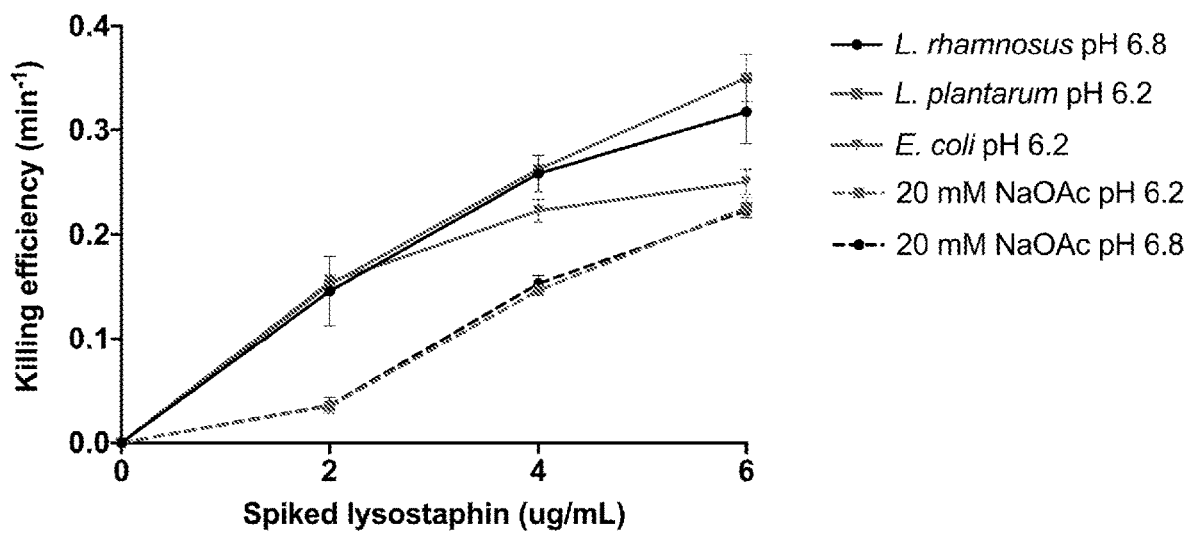
FIG. 7: Synergy effect on different bacterial strains. Measurements of *S. aureus* killing efficiency (1/IC50) for different bacterial lysates spiked with different concentrations of lysostaphin. A higher killing efficiency in bacterial lysate than in acetate buffer adjusted at equivalent pH is observed.

This synergistic effect between Lysostaphin and the L. rhamnosus lysate was observed for different concentrations of lysate (FIG. 6) and for different concentrations of Lysostaphin (FIG. 7).

To test if this effect was specific of L. rhamnosus lysate, S. aureus killing activity of Lysostaphin mixed with lysates from different bacteria (Lactobacillus plantarum and Escherichia coli) was measured. Synergistic effect was observed for both Lactobacillus plantarum and E. coli even if at high Lysostaphin concentration (60 µg/ml) E. coli lysate killing activity was similar to the activity in buffer (FIG. 7).

The inventors also tested if the pH of the lysate could explain this synergy as it is known that acidic pH is not optimum for Lysostaphin activity. Lysate from L. rhamnosus, L. plantarum and E. coli were respectively pH 6.8, 6.2, 6.2. S. aureus bactericidal activity was measured for different concentrations of Lysostaphin in acetate buffer with equivalent pH (6.2 and 6.8). A higher killing was still observed for the lysate compared to buffer at same pH (FIG. 7) indicating that the pH cannot explain the synergy observed.

Figure 8:
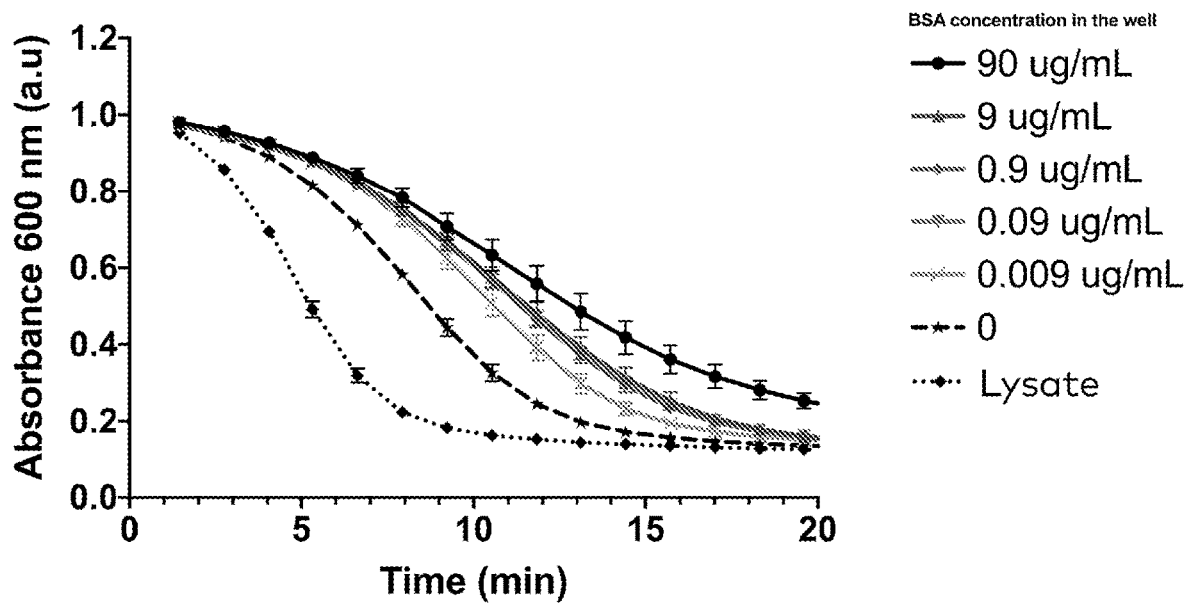
FIG. 8: Effect of molecular crowding on lysostaphin activity in acetate buffer. Measurements of *S. aureus* turbidity reduction in acetate buffer pH 5 with lysostaphin 4 µg/mL, supplemented with different concentrations of Bovine Serum Albumin (BSA) to increase molecular crowding, show a reduction in lysostaphin activity with higher molecular crowding.

One difference between Lysostaphin in acetate buffer and Lysostaphin in lysate is the presence of a large amount of proteins and other cellular molecules that might provide a high molecular crowding environment for Lysostaphin to act. In order to test if molecular crowding could explain the increased activity of Lysostaphin in bacterial lysate the inventors performed a turbidity reduction experiment in presence of increasing concentrations of Bovine Serum Albumin (BSA) (FIG. 8). All concentrations of BSA led to a slower decrease in turbidity indicating a lower Lysostaphin activity. Thus molecular crowding does not seem to explain the synergy effect observed between lysate and Lysostaphin.

The inventors have shown that a lysolysate, produced from the lysis of L. rhamnosus bacterial cells heterologously expressing cytoplasmic Lysostaphin, allows highly efficient and specific killing of S. aureus strains. Surprisingly inventors demonstrated a synergistic effect between Lysostaphin and L. rhamnosus lysate increasing Lysotaphin killing activity. This synergistic effect is not specific to L. rhamnosus lysate and depends on the lysate concentration.

Materials and Methods:
Bacterial Strains:

L. plantarum s15998 was isolated from fermented cabbage. Lysolysate was produced from strain s18195 (L. rhamnosus +p1016).

Production of Bacterial Lysates:

Overnight cultures of L. plantarum s15998 was inoculated from cryostock in 50 mL of MRS (NutriSelect Merck) and incubated in anaerobic conditions at 37° C. Overnight culture of L. rhamnosus was inoculated from cryostock in 50 mL of SPY2 (Heenan, C. N., et al.(2002). Lwt-Food Sci Technology 35, 171-176) and incubated in anaerobic conditions at 37° C. Overnight culture of E. coli K-12 MG1655 liquid culture was grown in LB (Difco) and incubated overnight in aerobic conditions at 37° C.

Overnight cultures were diluted 1/10 in 500 mL of the appropriate media pre-reduced in anaerobic conditions and incubated at 37° C. in anaerobic conditions except for E. coli that was incubated at 37° C. in aerobic conditions. At OD600 nm≈[1-2], bacterial cultures were put on ice, and following steps were performed at 4° C. First cells were washed twice in deionized water using centrifugation and finally resuspended in 12.5 mL of 20 mM acetate buffer pH 5 (40× concentration of the initial cell culture). The concentrated culture was then lysed using bead beating at 30 Hz for 2 cycles of 20 minutes, placing the sample on ice for 2 minutes in between cycles. Bacterial lysate was centrifuged for 10 min at 10 000 g and supernatant was then filtered (0.4 µm) and stored at 4° C. CFU was performed before and after bead beating treatment to measure lysis efficiency.

Production of Lysolysate:

Overnight culture of L. rhamnosus+p1016 was inoculated from cryostock in 50 mL of SPY2 medium (Heenan, C. N., et al. (2002). Lwt-Food Sci Technology 35, 171-176) with erythromycin at final concentration 5 µg/mL and incubated in anaerobic conditions at 37° C. Overnight culture was diluted 1/10 in 500 mL of SPY2 medium pre-reduced in anaerobic conditions and incubated at 37° C. in anaerobic conditions. At $OD_{600nm}$=0.3 the culture was induced with 200 ng/mL of inducing peptide IP-673 (Novopro Cat. #: 300935) and incubated at 37° C. until $OD_{600nm}$=1.0. Bacterial culture was put on ice, and every following step was performed at 4° C. First cells were washed twice in deionized water using centrifugation and finally resuspended in 12.5 mL of 20 mM acetate buffer pH 5 (40× concentration of the initial cell culture). The concentrated culture was then lysed using bead beating at 30 Hz for 2 cycles of 20 minutes, placing the sample on ice for 2 minutes in between cycles. Bacterial lysate was centrifuged for 10 min at 10 000 g and supernatant was then filtered (0.4 µm) and stored at 4° C. Measure of CFU was performed before and after bead beating treatment to measure lysis efficiency.

Turbidity Reduction Experiment:

Overnight culture of S. aureus strain Newman was inoculated from an isolated colony in 15 mL of TSB (Tryptic Soy Broth, Difco) and incubated at 37° C., aerobically. Overnight culture was diluted 1/100 in a final volume of 1.5 L of TSB and incubated aerobically at 37° C. At OD600 nm=1 culture was washed twice with deionised water at 4° C., centrifuged at 4° C., 4000 g for 10 minutes, resuspended in 7.5 mL of 1× PBS (Phosphate Buffered Saline, Fisher BioReagents, pH 7.4) and finally frozen as 500 µL aliquots at −20° C.

Bacterial suspension for the turbidity reduction assay was prepared from an aliquot of the frozen stock of S. aureus strain Newman. Lysostaphin solution and bacterial suspension were mixed in a ratio 1:10 in duplicates in a 96-well plate (Microlon 200, transparent, flat bottom) final volume 200 µL and absorbance at 600 nm (Tecan Infinite 200 pro) was measured every 1.3 minutes, at 37° C. without agitation for 1 hour.

EXAMPLE 2

Beneficial Effect of Lysate on Skin Microbiota

The approach of the inventors aims at killing specifically S. aureus, as shown in example 1, but also helping the skin commensal bacteria to restore homeostasis by helping them grow and occupe the niche left empty from S. aureus decolonization.

Figure 9:
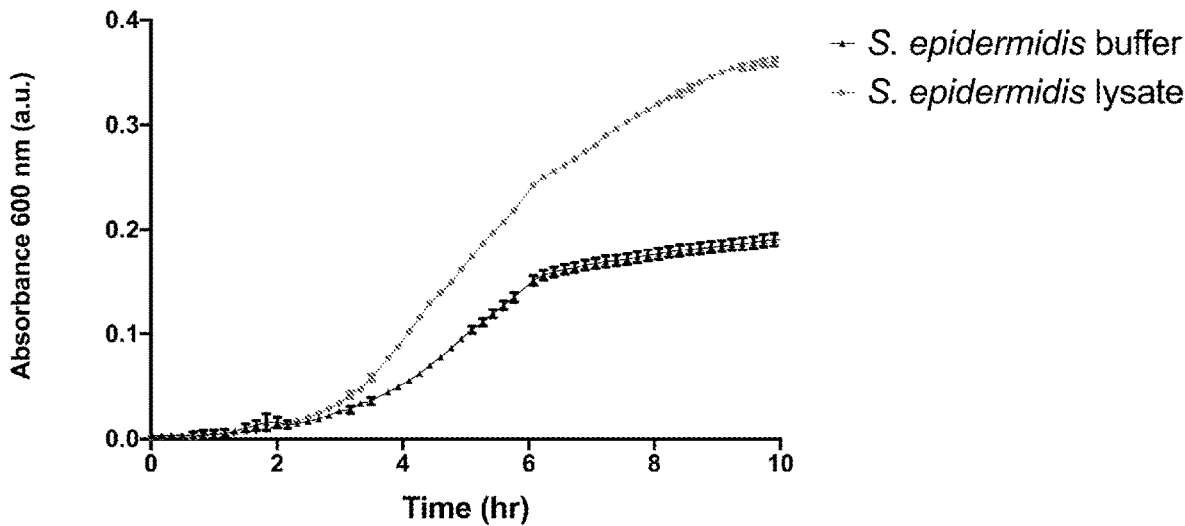
FIG. 9: Stimulation of *S. epidermidis* growth by *L. rhamnosus* lysate. Growth curve of *S. epidermidis* in diluted TSB (12.5% v/v) supplemented with 20 mM acetate buffer pH 5 or *L. rhamnosus* GG lysate

To test such an effect, the inventors investigated the effect of the lysate on the growth of S. epidermidis (FIG. 9). S. epidermidis (ATCC® 12228TM) was grown in poor nutrient conditions supplemented or not with L. rhamnosus lysate and cell density was followed by absorbance using OD600 nm. S. epidermidis shows a higher growth rate and final density in presence of *L. rhamnosus* lysate compared to buffer indicating a beneficial effect of the lysate on *S. epidermidis*.

Materials and Methods:

Production of *L. rhamnosus* Lysate:

Overnight culture of *L. rhamnosus* was inoculated from cryostock in 50 mL of SPY2 (Heenan, C. N., et al. (2002). Lwt-Food Sci Technology 35, 171-176) and incubated in anaerobic conditions at 37° C. Overnight culture was diluted 1/10 in 500 mL of the appropriate media pre-reduced in anaerobic conditions and incubated at 37° C. in anaerobic conditions. At OD600 nm≈1, bacterial culture was put on ice, and following steps were performed at 4° C. First cells were washed twice in deionized water using centrifugation and finally resuspended in 12.5 mL of 20 mM acetate buffer pH 5 (40× concentration of the initial cell culture). The concentrated culture was then lysed using bead beating at 30 Hz for 2 cycles of 20 minutes, placing the sample on ice for 2 minutes in between cycles. Bacterial lysate was centrifuged for 10 min at 10 000 g and supernatant was then filtered (0.4 µm) and stored at 4° C. CFU was performed before and after bead beating treatment to measure lysis efficiency.

Growth Curve Experiment:

A preculture of *S. epidermidis* (ATCC® 12228TM) was inoculated from cryostock into 5 mL TSB and incubated at 37° C. overnight. Overnight culture was resuspended, normalised to $OD_{600nm}=1$ and diluted 1/10 in 12.5% (v/v) TSB. In a 96 well plate, 180 µL of normalized bacterial culture was supplemented with 20 µL of *L. rhamnosus* lysate or 20 µL of 20 mM acetate buffer pH 5. Absorbance at 600 nm (Tecan Infinite 200 pro) was measured every 10 minutes, at 37° C. with agitation for a total of 6.8 hours.

EXAMPLE 3

*L. rhamnosus* Lysate is Non-Irritating and has Soothing Effect

Soothing effect of *L. rhamnosus* lysate on the skin of healthy volunteers submitted to mechanical stress via skin stripping was tested.

First a test was performed to test the irritating potential of the bacterial lysate. Briefly, three different *L. rhamnosus* lysate concentrations were put in contact with the skin of healthy volunteers during 48 hours. After 48 hours, *L. rhamnosus* lysates were removed from skin and skin reaction (erythema and oedema) was evaluated by a dermatologist 15 minutes, 1 hour and 24 hours after removal. These evaluations showed that the three different concentrations of *L. rhamnosus* lysate were non-irritating according to the amended Draize classification.

Figure 10:
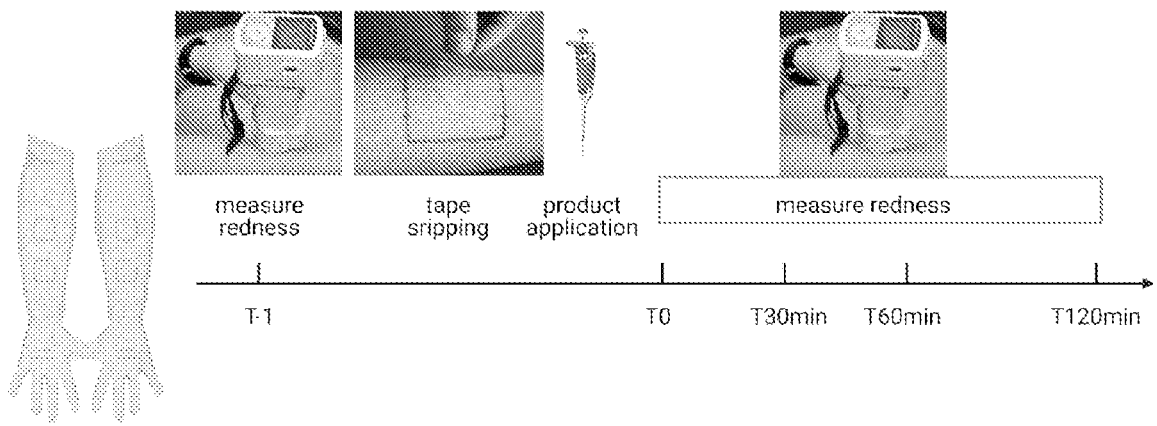
FIG. 10: Clinical protocol to evaluate soothing effect after skin stripping. At T-1 Redness parameter is measured using a colorimeter, tape stripping is performed several times to remove superficial layers of the skin and induce an increase in skin redness. Lysate is applied and as a placebo the 20 mM acetate buffer pH 5. Just after application the redness is measured at different time points. During this time the healthy volunteer is kept in a controlled environment with constant relative humidity and temperature.
Figure 11:
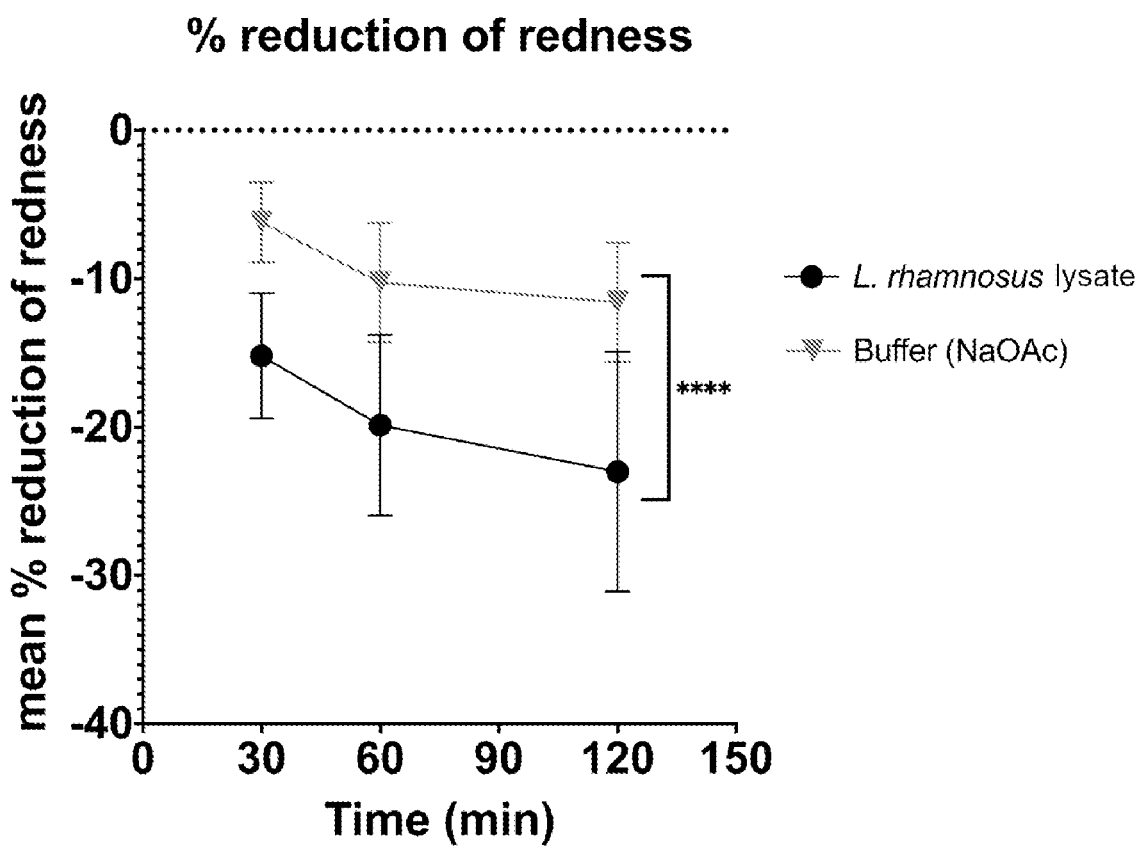
FIG. 11: Soothing effect of *L. rhamnosus* lysate. Mean percentage variation of redness after skin stripping (T0) on skin area treated with *L. rhamnosus* GG lysate or with 20 mM acetate buffer pH 5 (NaOAc). Paired t-test shows significant difference (p-value<0.0001) between both treatments at T=30, 60 and 120 min. % variation of redness= (skin redness T-skin redness T0)/skin redness T0.

To measure the soothing effect of the *L. rhamnosus* lysate, a mechanical stress was applied on the skin forearm of 20 volunteers by removing superficial layers of the skin (FIG. 10). Following skin stripping, the bacterial lysate and a placebo (20 mM acetate buffer pH 5) were applied in different treated zones. Redness of skin prior skin stripping (T-1), just after skin stripping (T0) and 30 min, 60 min, and 120 min after lysate and placebo applications was followed. A significant decrease in redness at all time after application (paired t-test p-value<0.0001 at T=30 min, T=60 min, T=120 min) was measured for *L. rhamnosus* lysate compared to the placebo control indicating a soothing effect of the *L. rhamnosus* lysate (FIG. 11).

Materials and Methods:

Production of *L. rhamnosus* lysate: 2L of *L. rhamnosus* culture was grown in MRS until OD600 nm=5,8. Centrifugation was performed at 10 000 g for 15 min and cells were resuspended in 200 mL of acetate buffer pH 5.

Cohort Recruitment for Skin Irritation Potential Test:

10 healthy female volunteers between 18 and 70 years old were informed about test purposes and were recruited under the supervision of a dermatologist.

Skin Irritation Potential Test:

The lysate was applied as it is using a Finn Chamber fixed to the skin with a tape already been tested for its safety to ensure the occlusive application of the product. The lysate was left in contact with the skin surface for 48 hours. The cutaneous reactions were analysed 15 minutes, one hour and 24 hours after Finn Chamber removal. A Finn Chamber containing a blotting paper disk soaked with demineralized water was applied and used as a negative control. For each experimental time, erythema reaction and oedema reaction were evaluated and their mean value combined to calculate a Mean Irritation Index (IIM) according to the amended Draize classification.

Cohort Recruitment for Skin Stripping Test:

20 healthy female volunteers between 18 and 70 years old were informed about test purposes and were recruited under the supervision of a dermatologist.

Skin Stripping Test:

4 skin areas on the volar surface of the forearms of each subject were stripped in order to induce transient and not harmful increase of skin redness. The skin stripping procedure consists in removing serial layers of stratum corneum by standardized repeated applications of adhesive tapes to the skin's surface. *L. rhamnosus* lysate was applied in one of the 4 surfaces and as a placebo the 20 mM acetate buffer pH 5 was also applied in another of the 4 surfaces. Skin redness was measured, using a colorimeter, at baseline (T-1, before stripping procedure), after stripping procedure (T0) and 30, 60 and 120 minutes after the single product applications.

Percentage variation=(skin redness T−skin redness T0)/skin redness T0.

In conclusion the engineered postbiotics of the present invention show multiple activities that once combined on human skin should help resolve dysbiosis-induced unaesthetic manifestations and reach homeostasis faster by:

killing specifically the most frequent aetiological agent that is *S. aureus*, without affecting the commensal skin population, stimulating growth of commensal skin population such as *S. epidermidis*, and having a soothing effect on the skin.

Some of these activities should act synergistically to address dysbiosis-induced unaesthetic manifestations.

The invention claimed is:

1. A method for killing unfavorable bacteria on a healthy skin and/or mucosa of a subject, comprising applying on said healthy skin and/or mucosa of said subject an engineered postbiotic composition comprising a microbial lysate and lysostaphin,
   wherein said microbial lysate and said lysostaphin have a synergistic effect in killing unfavorable bacteria on said healthy skin and/or mucosa of said subject.

2. The method according to claim 1, wherein said microbial lysate is obtained from GRAS and/or probiotic bacteria.

3. The method according to claim 1, wherein said microbial lysate is obtained from bacteria isolated from a subject.

4. The method according to claim 1, wherein said microbial lysate is obtained from *Lactobacillus rhamnosus* bacteria.

5. The method according to claim 1, wherein said microbial lysate is obtained from bacteria which do not comprise any antibiotic resistance marker.

6. The method according to claim 1, wherein said postbiotic composition comprises at least two different bacteriocins and/or endolysins.

7. The method according to claim 6, wherein said at least two different bacteriocins and/or endolysins target the same bacterial species.

8. The method according to claim 6, wherein said at least two different bacteriocins and/or endolysins target different bacterial species.

9. The method according to claim 1, wherein said engineered postbiotic composition stimulates growth of at least one commensal bacterial species of the subject.

10. The method according to claim 9, wherein said engineered postbiotic composition stimulates growth of at least one commensal bacterial species of the subject and said lysostaphin targets at least one unfavorable bacterial species.

11. A method for the care of sensitive, sensitized, fragile and/or weakened skin and/or mucosa, wherein an engineered postbiotic composition is applied on said sensitive, sensitized, fragile and/or weakened skin and/or mucosa, wherein said engineered postbiotic composition comprises a microbial lysate and lysostaphin, wherein said microbial lysate and said lysostaphin have a synergistic effect in killing unfavorable bacteria on said sensitive, sensitized, fragile and/or weakened skin and/or mucosa of said subject.

12. The method according to claim 11, for the care of unaesthetic and/or unpleasant and/or uncomfortable manifestations of sensitive, sensitized, fragile and/or weakened skin and/or mucosa, wherein said engineered postbiotic is applied on the skin and/or mucosa of a subject with unaesthetic and/or unpleasant and/or uncomfortable manifestations of sensitive, sensitized, fragile and/or weakened skin and/or mucosa.

13. The method according to claim 11, wherein the unaesthetic and/or unpleasant and/or uncomfortable manifestations of sensitive, sensitized, fragile and/or weakened skin and/or mucosa are chosen from the feeling of heat or warmth or tension, tingling, stinging, tightness, itching, pruritus, dry patches, erythema, redness and a mixture of these manifestations.

14. The method according to claim 1, for controlling and/or reducing body odor, wherein said engineered postbiotic composition is applied on the skin of the feet or the skin of the armpits.

15. The method according to claim 1, wherein said engineered postbiotic composition is in the form of a cosmetic formulation for topical application.

* * * * *